(12) United States Patent
Grouchy et al.

(10) Patent No.: US 11,062,792 B2
(45) Date of Patent: Jul. 13, 2021

(54) DISCOVERING GENOMES TO USE IN MACHINE LEARNING TECHNIQUES

(71) Applicant: Analytics For Life Inc., Kingston (CA)

(72) Inventors: Paul Grouchy, Toronto (CA); Timothy Burton, Ottowa (CA); Ali Khosousi, Toronto (CA); Abhinav Doomra, North York (CA); Sunny Gupta, Toronto (CA); Ian Shadforth, Morrisville, NC (US)

(73) Assignee: Analytics For Life Inc., Toronto (CA)

( * ) Notice: Subject to any disclaimer, the term of this patent is extended or adjusted under 35 U.S.C. 154(b) by 969 days.

(21) Appl. No.: 15/653,441

(22) Filed: Jul. 18, 2017

(65) Prior Publication Data
US 2019/0026431 A1    Jan. 24, 2019

(51) Int. Cl.
G06N 3/08      (2006.01)
G16B 40/00    (2019.01)
G16B 5/00      (2019.01)
G06N 20/20    (2019.01)
G06N 3/12      (2006.01)
(Continued)

(52) U.S. Cl.
CPC ............. *G16B 40/00* (2019.02); *G01N 33/50* (2013.01); *G06F 16/00* (2019.01); *G06N 3/126* (2013.01); *G06N 20/20* (2019.01); *G16B 5/00* (2019.02); *G06F 19/00* (2013.01); *G06N 3/086* (2013.01); *G06N 5/003* (2013.01); *G06N 20/10* (2019.01)

(58) Field of Classification Search
None
See application file for complete search history.

(56) References Cited

U.S. PATENT DOCUMENTS 5,148,513 A * 9/1992 Koza .................. G06N 3/126
                                                706/13
6,513,025 B1   1/2003 Rosen
(Continued)

FOREIGN PATENT DOCUMENTS

CN    101785672 A    7/2010
CN    103177114 A    6/2013
(Continued)

OTHER PUBLICATIONS

Bach et al., "Interactive Random Graph Generrration with Evolutionary Algorithms", 2013, Springer-Verlag Berlin Heidelberg, all pages (Year: 2013).*
(Continued)

*Primary Examiner* — Daniel C Puentes
(74) *Attorney, Agent, or Firm* — Perkins Coie LLP

(57) ABSTRACT

A facility for identifying combinations of feature and machine learning algorithm parameters, where each combination can be combined with one or more machine learning algorithms to train a model, is disclosed. The facility evaluates each genome based on the ability of a model trained using that genome and a machine learning algorithm to produce accurate results when applied to a validation data set by, for example, generating a fitness or validation score for the trained model and the corresponding genome used to train the model. Genomes that produce fitness scores that exceed a fitness threshold are selected for mutation, mutated, and the process is repeated. These trained models can then be applied to new data to generate predictions for the underlying subject matter.

26 Claims, 8 Drawing Sheets

(51) Int. Cl.
    *G06F 16/00*    (2019.01)
    *G01N 33/50*    (2006.01)
    *G06N 20/10*    (2019.01)
    *G06N 5/00*     (2006.01)
    *G06F 19/00*    (2018.01)

(56) References Cited

U.S. PATENT DOCUMENTS

| | | |
|---|---|---|
| 7,480,640 B1 | 1/2009 | Elad et al. |
| 7,792,770 B1 | 9/2010 | Phoha et al. |
| 7,827,011 B2 | 11/2010 | DeVaul et al. |
| 8,016,200 B2 | 10/2011 | Kirby et al. |
| 8,041,651 B2 | 10/2011 | Greer |
| 8,065,247 B2 | 11/2011 | Schlottmann |
| 8,340,746 B2 | 12/2012 | Syed et al. |
| 8,510,245 B2 | 8/2013 | Stojadinovic et al. |
| 8,521,488 B2 | 8/2013 | Kirby et al. |
| 8,688,603 B1 | 4/2014 | Kurup et al. |
| 9,173,614 B2 | 11/2015 | Sternickel et al. |
| 9,239,986 B2 | 1/2016 | Lin et al. |
| 9,245,235 B2 | 1/2016 | Chen et al. |
| 9,336,484 B1 | 5/2016 | Iverson |
| 9,349,178 B1 | 5/2016 | Itu et al. |
| 9,367,683 B2 | 6/2016 | Kolacinski et al. |
| 9,576,262 B2 | 2/2017 | Ganguly et al. |
| 9,582,781 B1 | 2/2017 | Kearns et al. |
| 9,652,354 B2 | 5/2017 | Filimonov et al. |
| 9,689,874 B2 | 6/2017 | Blume et al. |
| 9,697,469 B2 | 7/2017 | McMahon et al. |
| 9,811,795 B1 | 11/2017 | Kearns et al. |
| 9,864,956 B1 | 1/2018 | Sai |
| 9,910,980 B2 | 3/2018 | Kolacinski et al. |
| 10,127,214 B2 | 11/2018 | Munro et al. |
| 10,366,346 B2 | 7/2019 | Achin et al. |
| 10,405,219 B2 | 9/2019 | Feldkamp |
| 10,417,523 B2 | 9/2019 | Singh et al. |
| 2003/0018595 A1* | 1/2003 | Chen .................. G06K 9/6228 706/12 |
| 2003/0088565 A1 | 5/2003 | Walter et al. |
| 2004/0204957 A1 | 10/2004 | Afeyan et al. |
| 2005/0198182 A1* | 9/2005 | Prakash ............... G06Q 10/107 709/206 |
| 2006/0230006 A1 | 10/2006 | Buscema |
| 2007/0047811 A1 | 3/2007 | Itoh et al. |
| 2010/0030780 A1 | 2/2010 | Eshghi et al. |
| 2010/0063948 A1 | 3/2010 | Virkar et al. |
| 2011/0119213 A1 | 5/2011 | Elisseeff et al. |
| 2011/0172514 A1 | 7/2011 | Lee et al. |
| 2012/0029974 A1 | 2/2012 | Councill et al. |
| 2012/0040861 A1* | 2/2012 | Williams ............ G01N 33/6893 506/9 |
| 2012/0078097 A1 | 3/2012 | Wang et al. |
| 2013/0085773 A1 | 4/2013 | Yao et al. |
| 2013/0103620 A1 | 4/2013 | Yoon et al. |
| 2014/0143188 A1 | 5/2014 | Mackey et al. |
| 2014/0344208 A1 | 11/2014 | Ghasemzadeh et al. |
| 2014/0351183 A1 | 11/2014 | Germain et al. |
| 2015/0003704 A1 | 1/2015 | Nomura et al. |
| 2015/0127595 A1 | 5/2015 | Hawkins, III et al. |
| 2015/0134315 A1 | 5/2015 | Sarmiento et al. |
| 2016/0045120 A1 | 2/2016 | Friedman et al. |
| 2016/0055426 A1 | 2/2016 | Aminzadeh et al. |
| 2016/0180247 A1 | 6/2016 | Li et al. |
| 2016/0300036 A1 | 10/2016 | Ramazzotti et al. |
| 2016/0300156 A1 | 10/2016 | Bowers et al. |
| 2016/0314580 A1 | 10/2016 | Lloyd et al. |
| 2016/0350671 A1 | 12/2016 | Morris, II et al. |
| 2017/0017900 A1 | 1/2017 | Maor et al. |
| 2017/0169180 A1 | 6/2017 | Hamann et al. |
| 2017/0249434 A1 | 8/2017 | Brunner |
| 2018/0032678 A1 | 2/2018 | Dandala et al. |
| 2018/0039731 A1 | 2/2018 | Szeto |
| 2018/0060324 A1 | 3/2018 | Clinton et al. |
| 2018/0137415 A1 | 5/2018 | Steinberg et al. |
| 2018/0225391 A1 | 8/2018 | Sali et al. |
| 2018/0293501 A1 | 10/2018 | Ambati et al. |
| 2018/0349555 A1 | 12/2018 | Devarakonda et al. |
| 2019/0080240 A1 | 3/2019 | Andoni et al. |
| 2019/0087469 A1 | 3/2019 | Zhang et al. |
| 2019/0130277 A1 | 5/2019 | Andoni et al. |
| 2019/0138946 A1 | 5/2019 | Asher et al. |
| 2019/0146759 A1 | 5/2019 | Chiang et al. |
| 2019/0188536 A1 | 6/2019 | Lei et al. |
| 2019/0200893 A1 | 7/2019 | Grouchy et al. |
| 2019/0219994 A1 | 7/2019 | Yan et al. |
| 2019/0295000 A1 | 9/2019 | Candel et al. |

FOREIGN PATENT DOCUMENTS

| | | |
|---|---|---|
| CN | 105843896 A | 8/2016 |
| CN | 105912500 A | 8/2016 |
| CN | 106777891 A | 5/2017 |
| CN | 107993723 A | 5/2018 |
| CN | 108090570 A | 5/2018 |
| CN | 108335756 A | 7/2018 |
| CN | 108875815 A | 11/2018 |
| CN | 108960269 A | 12/2018 |
| CN | 109117864 A | 1/2019 |
| CN | 109146076 A | 1/2019 |
| CN | 109217291 A | 1/2019 |
| CN | 109242021 A | 1/2019 |
| CN | 109273094 A | 1/2019 |
| CN | 109635955 A | 4/2019 |
| CN | 109711558 A | 5/2019 |
| CN | 109828836 A | 5/2019 |
| CN | 109948668 A | 6/2019 |
| CN | 110175644 A | 8/2019 |
| EP | 3048563 A | 7/2016 |
| JP | 2019079392 A | 5/2019 |
| KR | 20190078850 A | 7/2019 |
| WO | 2005036180 | 4/2005 |
| WO | 2005048185 A1 | 5/2005 |
| WO | 2007044944 | 4/2007 |
| WO | 2009063463 | 5/2009 |
| WO | 2010044683 A1 | 4/2010 |
| WO | 2012103290 | 8/2012 |
| WO | 2012103290 A1 | 8/2012 |
| WO | 2016022438 A1 | 2/2016 |
| WO | 2016057001 A1 | 4/2016 |
| WO | 2016118513 A1 | 7/2016 |
| WO | 2016164680 A1 | 10/2016 |
| WO | 2016187711 A1 | 12/2016 |
| WO | 2017033164 | 3/2017 |
| WO | 2017053347 A1 | 3/2017 |
| WO | 2017059022 A1 | 4/2017 |
| WO | 2017120579 A1 | 7/2017 |
| WO | 2007147166 A1 | 12/2017 |
| WO | 2019129060 A1 | 7/2019 |
| WO | 2019179836 A1 | 9/2019 |

OTHER PUBLICATIONS

Alhoniemi, E., et al., "Compact Modeling of Data Using Independent Variable Group Analysis," IEEE Trans. on Neural Networks 18.6 (2007):1762-1776.

Alonso et al., "Modelling Medical Time Series Using Grammar-Guided Genetic Programming," Industrial Conf. on Data Mining, Springer, 2008.

Araújo, "A New Evolutionary Morphological-Rank-Linear Approach for Time Series Prediction," IEEE Congress on Evolutionary Computation, CEC 2007, IEEE, 2007.

Arnaldo, I. et al., "Building Predictive Models via Feature Synthesis," Gecco '15, ACM, 2015, pp. 983-990.

Bishop, Christopher M., "Pattern Recognition and Machine Learning," Springer Science+Business Media, LLC, 2006, 758 pages.

Czajkowski et al., "An Evolutionary Algorithm for Global Induction of Regression Trees with Multivariate Linear Models," ISMIS 2011, LNAI 6804, pp. 230-239, 2011, Springer-Verlag.

Grosman et al., "Adaptive Genetic Programming for Steady-State Process Modeling," Computers & Chemical Engineering 28.12 (2004): 2779-2790, Elsevier.

(56) References Cited

OTHER PUBLICATIONS

Hadavandi et al., "Integration of Genetic Fuzzy Systems and Artificial Neural Networks for Stock Price Forecasting," Knowledge-Based Systems 23.8 (2010): 800-808, Elsevier.

Karabulut, E.M. and T. Ibrikci, "Analysis of Cardiotocogram Data for Fetal Distress Determination by Decision Tree Based Adaptive Boosting Approach," Journal of Computer and Communications, Scientific Research, published online Jul. 2014, pp. 32-37.

Spector, L. et al., "Evolution Evolves with Autoconstruction," ECADA 2016, ACM, 2016, pp. 1349-1356.

Tolstikhin et al., "AdaGAN: Boosting Generative Models," arXiv preprint, arxiv.org, arXiv:1701.02386 (2017), Jan. 9, 2017, https://arxiv.org/pdf/1701.02386.pdf.

Tuv, E. et al., "Feature Selection with Ensembles, Artificial Variables, and Redundancy Elimination," Journal of Machine Learning Research 10 (2009): 1341-1366.

Valdes, J., "Similarity-Based Neuro-Fuzzy Networks and Genetic Algorithms in Time Series Models Discovery," NRC/ERB-1093, NRC 44919, National Research Council of Canada, 2002.

Welling, M. et al., "Self Supervised Boosting," NIPS, 2002, pp. 665-672.

International Search Report and Written Opinion received for related International Patent Application No. PCT/IB2018/000902, dated Dec. 6, 2018, 17 pages.

Quade et al., "Prediction of Dynamical Systems by Symbolic Regression", Physical Review E 94(1), Jul. 2016 (16 pages).

International Search Report and Written Opinion received for counterpart International Patent Application No. PCT/IB2018/000929, dated Jan. 7, 2019 (8 pages).

Abdel-Aal R.E., "GMDH-based Feature Ranking and Selection for Improved Classification of Medical Data." Journal of Biomedical Informatics 38 (2005) 456-468. © 2005 Elsevier Inc. (13 pages).

Bach, Benjamin, et al., "Interactive Random Graph Generation with Evolutionary Algorithms." W. Didimo and M. Patrignani (Eds.): GD 2012, LNCS 7704, pp. 541-552, 2013. © Springer-Verlag Berlin Heidelberg 2013. (12 pages).

Bishop, Christopher M., "Pattern Recognition and Machine Learning." © 2006 Springer Science+Business Media, LLC. (758 pages).

Abdel-Aal R.E., "Improved Classification of Medical Data Using Abductive Network Committees Trained on Different Feature Subsets." Research Institute and the Department of Computer Engineering at King Fahd University of Petroleum and Minerals, Dhahran, Saudi Arabia. (33 pages).

Extended European Search Report received for counterpart European Patent Application No. 18834730_6, mailed Apr. 21, 2021 (13 pp.).

Samanta B et al: "Artificial Neural Networks and Genetic Algorithm for Bearing Fault Detection," Soft 7,'Omputing; a Fusion of Foundations, Methodologies and APPLICATIONS_ Springer, Berlin De, vol. 10, no. 3, 1 Feb. 2006 (2006-02-01), pp. 264-271, XP019348667.

Sachnev Vasily et al: "Parkinson Disease Classification Based on Binary Coded Genetic Algorithm and Extreme _earning Machine," 2014 IEEE Ninth International Conference on Intelligent Sensors, Sensor Nietvvorks and Information Processing (Issnip). IEEE, 21 Apr. 2014 (2014-04-21), pp. 1-6, )(P032604443.

3HARDWAJ Arpit et al: "A Novel Genetic Programming Approach for Epileptic Seizure Detection," Computer Methods and Programs in Biomedicine, Elsevier, Amsterdam, Nl, vol. 124, 2 Nov. 2015 (2015-11-02), pp. 2-18, XP029384416.

Extended European Search Report received for related European Patent Application No. 18835234.8, mailed Mar. 22, 2021 (17 pp.).

Szerlip, Paul a. et al., "Unsupervised Feature Learning through Divergent Discriminative Feature Accumulation" roceedings of the Twenty-Ninth Aaai Conference on Artificial Intelligence (Aaai-2015), Jan. 30, 2015. ages 2979-2985, XP055585712. Retrieved from the Internet Url:https://eplex.cs.uctedu/papers/szerlip_aaai15.pdf :retrieved on May 6, 2019).

Nsir U. et al., "literature Review on Feature Selection -Methods for HighlAmensionaiData,"-Intemational Journal of 3omputer Applications, [Online] vol. 136, No. 1, Feb. 17, 2016. Pages 9-17, XP055783802, Doi: 10.5120/ jca2016908317. Retrieved from the Internet: Url:https-J/www.researchgate_net/profile/Asir-Antony-Danasingh/ Dublication/295472880_Literature_Review on_Feature_Selection_Methods _for High-Dimensional Data/ inks/ 57b697a108ae19a365fc59d0fLiterature-Review-on-Feature-Selection-Methods-for-High-Dimensional-Data.pdf> (retrieved on Aug. 19, 2016).

* cited by examiner

DISCOVERING GENOMES TO USE IN MACHINE LEARNING TECHNIQUES

RELATED APPLICATIONS

This application is related to U.S. patent application Ser. No. 13/970,580, filed on Aug. 19, 2013, entitled "NON-INVASIVE METHOD AND SYSTEM FOR CHARACTERIZING CARDIOVASCULAR SYSTEMS," now U.S. Pat. No. 9,289,150; U.S. patent application Ser. No. 15/061,090, filed on Mar. 4, 2016, entitled "NON-INVASIVE METHOD AND SYSTEM FOR CHARACTERIZING CARDIOVASCULAR SYSTEMS;" U.S. patent application Ser. No. 15/588,148, filed on May 5, 2017, entitled "NON-INVASIVE METHOD AND SYSTEM FOR CHARACTERIZING CARDIOVASCULAR SYSTEMS;" U.S. patent application Ser. No. 13/605,364, filed on Sep. 6, 2012, entitled "SYSTEM AND METHOD FOR EVALUATING AN ELECTROPHYSIOLOGICAL SIGNAL," now U.S. Pat. No. 8,923,958; U.S. patent application Ser. No. 13/970,582, filed on Aug. 19, 2013, entitled "NON-INVASIVE METHOD AND SYSTEM FOR CHARACTERIZING CARDIOVASCULAR SYSTEMS FOR ALL-CAUSE MORTALITY AND SUDDEN CARDIAC DEATH RISK," now U.S. Pat. No. 9,408,543; U.S. patent application Ser. No. 15/207,214, filed on Jul. 11, 2016, entitled "NON-INVASIVE METHOD AND SYSTEM FOR CHARACTERIZING CARDIOVASCULAR SYSTEMS FOR ALL-CAUSE MORTALITY AND SUDDEN CARDIAC DEATH RISK;" U.S. patent application Ser. No. 14/295,615, filed on Jun. 4, 2014, entitled "NONINVASIVE ELECTROCARDIOGRAPHIC METHOD FOR ESTIMATING MAMMALIAN CARDIAC CHAMBER SIZE AND MECHANICAL FUNCTION;" U.S. patent application Ser. No. 14/077,993, filed on Nov. 12, 2013, entitled "NONINVASIVE ELECTROCARDIOGRAPHIC METHOD FOR ESTIMATING MAMMALIAN CARDIAC CHAMBER SIZE AND MECHANICAL FUNCTION;" U.S. patent application Ser. No. 14/596,541, filed on Jan. 14, 2015, entitled "NONINVASIVE METHOD FOR ESTIMATING GLUCOSE, GLYCOSYLATED HEMOGLOBIN AND OTHER BLOOD CONSTITUENTS," now U.S. Pat. No. 9,597,021; U.S. patent application Ser. No. 15/460,341, filed on Mar. 16, 2017, entitled "NONINVASIVE METHOD FOR ESTIMATING GLUCOSE, GLYCOSYLATED HEMOGLOBIN AND OTHER BLOOD CONSTITUENTS;" U.S. patent application Ser. No. 14/620,388, filed on Feb. 12, 2015, entitled "METHOD AND SYSTEM FOR CHARACTERIZING CARDIOVASCULAR SYSTEMS FROM SINGLE CHANNEL DATA;" U.S. patent application Ser. No. 15/192,639, filed on Jun. 24, 2016, entitled "METHODS AND SYSTEMS USING MATHEMATICAL ANALYSIS AND MACHINE LEARNING TO DIAGNOSE DISEASE;" U.S. patent application Ser. No. 15/248,838, filed on Aug. 26, 2016, entitled "BIOSIGNAL ACQUISITION DEVICE;" U.S. Provisional Patent Application No. 62/397,895, filed on Sep. 21, 2016, entitled "GRAPHICAL USER INTERFACE FOR CARDIAC PHASE-SPACE TOMOGRAPHY;" U.S. patent application Ser. No. 15/633,330, filed Jun. 26, 2017, entitled "NON-INVASIVE METHOD AND SYSTEM FOR MEASURING MYOCARDIAL ISCHEMIA, STENOSIS IDENTIFICATION, LOCALIZATION AND FRACTIONAL FLOW RESERVE ESTIMATION;" and U.S. patent application Ser. No. 15/653,433, filed concurrently herewith, entitled "DISCOVERING NOVEL FEATURES TO USE IN MACHINE LEARNING TECHNIQUES, SUCH AS MACHINE LEARNING TECHNIQUES FOR DIAGNOSING MEDICAL CONDITIONS." Each of the above-identified applications and issued patents is hereby incorporated by reference in its entirety.

BACKGROUND

Machine learning techniques predict outcomes based on sets of input data. For example, machine learning techniques are being used to predict weather patterns, geological activity, provide medical diagnoses, and so on. Machine learning techniques rely on a set of features generated using a training set of data (i.e., a data set of observations, in each of which an outcome to be predicted is known), each of which represents some measurable aspect of observed data, to generate and tune one or more predictive models. For example, observed signals (e.g., heartbeat signals from a number of subjects) may be analyzed to collect frequency, average values, and other statistical information about these signals. A machine learning technique may use these features to generate and tune a model that relates these features to one or more conditions, such as some form of cardiovascular disease (CVD), including coronary artery disease (CAD), and then apply that model to data sources with unknown outcomes, such as an undiagnosed patient or future weather patterns, and so on. Conventionally, these features are manually selected and combined by data scientists working with domain experts.

DETAILED DESCRIPTION

Figure 1:
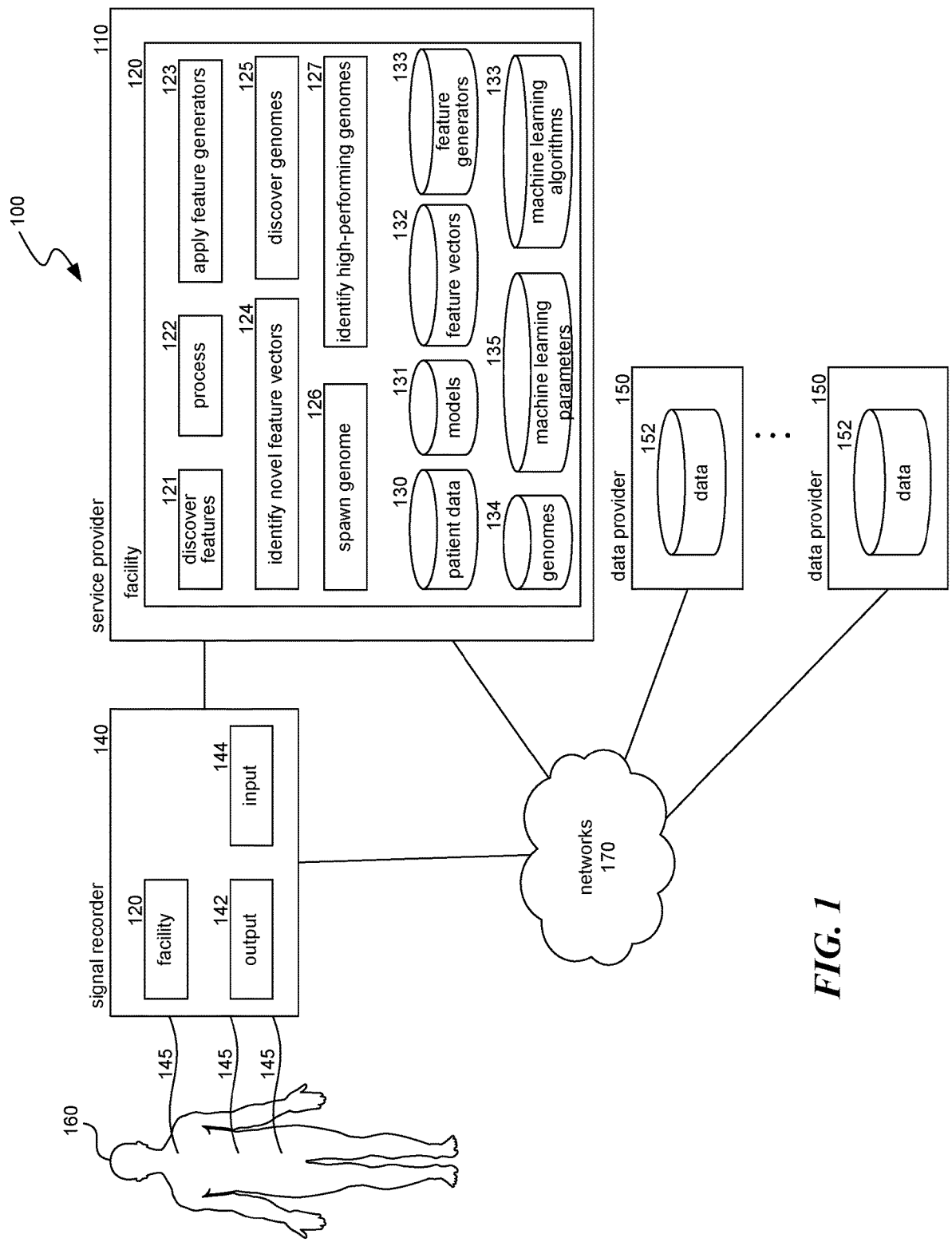
FIG. 1 is a block diagram illustrating an environment in which the facility operates in some embodiments.

Because machine learning techniques rely on features and/or combinations of features, the process of feature selection and combination typically is an important part of a machine learning process. Moreover, because a large number of diverse machine learning algorithms exist (e.g., decision trees, artificial neural networks (ANNs), deep ANNs, genetic (and meta-genetic) algorithms, and so on), the choice of algorithm and any associated parameters can also be important. For example, different machine learning algorithms (or family of machine learn algorithms) may be best suited for different types of data and/or the types of predictions to be made. Furthermore, different machine learning algorithms may present various tradeoffs with respect to resources (e.g., memory, processor utilization), speed, accuracy, and so on. Typically, models are trained using machine learning algorithms, features, and parameters selected by individuals based on the preferences of those individuals and/or criteria specified by those individuals. The inventors have recognized that it can be expensive and time-consuming manually to identify features, machine learning algorithms, and corresponding parameters and even more difficult to produce features, machine learning algorithms, and corresponding parameters that produce more accurate models and, therefore, more accurate predictions. Accordingly, the inventors have conceived and reduced to practice a facility that performs automatic discovery of combinations of features, machine learning algorithms, and/or machine learning parameters.

In some embodiments, the facility operates as part of a machine learning pipeline that constructs and evaluates predictive models, such as those for disease diagnosis, based on time-series and/or other signals, such as physiological signals. The machine learning process uses features to identify patterns within a training set of data and, based on these patterns, generates predictive models. These predictive models can be validated using validation data sets (i.e., data sets for which an outcome is known but that were not used to train the model) and applied to new input data in order to predict outcomes from the input data, such as providing a diagnosis for a medical condition, etc. As new data and new features are produced or acquired, the machine learning process improves upon the predictive capabilities of these models by incorporating new features and, in some cases, discarding others, such as those that are determined to be too similar to other features.

In particular, the facility seeks to identify combinations of features and machine learning algorithm parameters where each combination can be used to train one or more models. A combination of features and/or machine learning parameters is sometimes referred herein to as a "genome." The facility evaluates each genome based on the ability of a model trained using a machine learning algorithm and that genome to produce accurate results when applied to a validation data set by, for example, generating a fitness or validation score for the trained model and the corresponding genome used to train the model. In some cases, the facility uses the validation score as a fitness score while in other cases the validation score is an element of a fitness score (e.g., fitness score=training score+validation score). In some cases, multiple models may be trained using a genome and the resulting fitness scores can be aggregated to generate an aggregated fitness score for the genome.

By way of example, the facility for identifying combinations of features and machine learning algorithm parameters can be used for a medical diagnosis predictive modeling task. In this example, the facility receives, for a number of patients or subjects, one or more sets of physiological data that relate to some type of physiological output or condition of the patient over a period of time (e.g., less than a second, on the order of a few seconds, about ten seconds, about 30 seconds and up to about five minutes, about an hour or more, etc.), such as electroencephalograms, and so on. These data may be received in real-time or near real-time, concurrent or nearly concurrent with the operation of the facility, or they may be received at an earlier time. In some cases, the facility discards certain portions of the signal to ensure that the signals from each patient commence at a stable and consistent initial condition. Furthermore, the data may be normalized to remove potentially misleading information. For example, the facility can normalize the amplitude of signal data (e.g., transforming to a z-score), to account for variations in signal strength caused by sensor contact or other non-physiological data. As another example, in the case of a cardiac signal, the facility can perform a peak search and discard any data before a first heartbeat identified in the signal and after a last heartbeat identified in the signal.

In some embodiments, the facility applies a set of feature generators to a set of signals to generate, for each combination of a signal and a feature generator, a feature value for the signal. Thus, each feature value is representative of some property of the underlying signal data. In one example, the facility receives patient data for each of 1000 patients and applies one or more feature generators to the data to generate, for each application of a feature generator to the data of a single patient, a feature value (or set of feature values). The facility collects the feature values generated by a single feature generator in a "feature vector," such that the feature vector stores one feature value per patient. Once the feature vectors are generated, they can be compared to determine how different each is relative to each of the other feature vectors. The facility computes a distance metric for each feature vector to assess the novelty of the corresponding feature generator. Based on the assessed novelty, the facility (1) provides the feature generators that produced the novel feature vectors to the machine learning process for the purpose of basing new predictive models on the provided feature generators and (2) modifies these feature generators to create a new generation of feature generators. The facility repeats this evolutionary process to identify even more novel features for use by the machine learning process.

In some embodiments, for each received set of data, the facility computes or identifies separate sets of one or more values from the data. For example, in the case of data generated as part of an electrocardiogram, the facility identifies global and local maxima and minima within the data, computes frequency/period information from the data, calculates average values of the data over a certain period of time (e.g., the average duration and values generated during a QRS complex), and so on. In some cases, the facility transforms the received data and extracts sets of one or more values from the transformed data. The facility can transform received signal data in any number of ways, such as taking one or more (successive) derivatives of the data, taking one or more partial derivatives of the data, integrating the data, calculating the gradient of the data, applying a function to the data, applying a Fourier transform, applying linear or matrix transformations, generating topology metrics/features, generating computational geometry metrics/features, generating differential manifold metrics/features, and so on. In this manner, the facility generates multiple perspectives of the data in order to yield a diverse set of features. While these transformations are provided by way of example, one of ordinary skill will recognize that the data can be transformed in any number of ways.

In one example, the facility receives multiple input signals (e.g., input signals collected by different electrodes or leads connected to a patient, multimodal signals, such as signals from leads of wide-band biopotential measuring equipment and a channel of $S_pO_2$ (blood oxygen saturation), and so on) and/or transformed signals and extracts values from the signal data by computing, for each signal, an average value of the signal over the sampling period. In this example, four signals per patient are represented, although one of ordinary skill in the art will recognize that any number of signals may be monitored and/or received for processing and further analysis by the facility. Thus, in this example, the extracted data of each patient can be represented as a set of these average values over time, such as:

TABLE 1

| Patient | A | B | C | D |
|---|---|---|---|---|
| 1 | 0.24 | 0 | 0 | 30 |
| 2 | 0.2 | 0.6 | 4.2 | 5 |
| ... | ... | ... | ... | ... |
| n | .32 | 2 | 4 | .02 |

Table 1 represents a set of average signal values (A, B, C, and D) for each of n patients. Although average values have been used here, one of ordinary skill in the art will recognize that any type of data can be extracted or computed from the underlying data signals, such as the amount of time that a signal exceeded a threshold value, the values for one signal while the value of another signal exceeded a threshold value, and so on.

In some embodiments, after data have been extracted from the received signal, the facility applies one or more feature generators to the received or generated data, such as the extracted data, the raw or preprocessed signal data, the transformed data, and so on. A feature generator receives as input at least a portion or representation of the signal data and produces a corresponding output value (or set of values) (i.e., a "feature"). One set of feature generators includes the following equations:

$$F1 = A + C - D, \qquad (Eq\ 1)$$

$$F2 = \frac{A * S(4) * B}{D} + C + \sqrt{D},\ \text{and} \qquad (Eq\ 2)$$

$$F3 = S(1) * D, \qquad (Eq\ 3)$$

where each of A, B, C, and D represents a value extracted from a specific patient's data and S(t) represents, for each signal, the value of the signal at time t. In Eq 1, for example, F1 represents the name of the feature while the equation A+C−D represents the corresponding feature generator. In some cases, the facility employs composite feature generators in which one feature generator serves as an input to another feature generator, such as:

$$F4 = \frac{F1 * F2}{\sqrt[3]{F3}} + .057 \qquad (Eq\ 4)$$

In this example, the facility applies feature generators to the extracted data of each patient represented in Table 1 to generate, for each feature generator, a feature vector of three values (one for each patient), such as those represented in Table 2 below:

TABLE 2

| Patient | F1 | F2 | F3 |
|---|---|---|---|
| 1 | −29.76 | 5.48 | 905.83 |
| 2 | −0.6 | 6.67 | 9.57 |
| ... | ... | ... | ... |
| n | 4.3 | 185.74 | 0.04 |

In this example, the facility has applied each feature generator F1, F2, and F3 to the extracted data shown in Table 1 to generate, for each feature generator, a corresponding feature vector that includes a value for each patient. For example, the feature vector generated by applying feature generator F1 to the extracted data includes a value of −29.76 for Patient 1, a value of −0.6 for patient 2, and so on. Thus, each feature vector represents, for a specific feature generator, a signature (not necessarily unique) for the corresponding feature generator based on at least a portion of each patient's physiological data (i.e., the patients represented in the physiological data to which the feature generators were applied). In some examples, feature generators are expressed using different structures or models, such as expression trees, neural networks, etc. One of ordinary skill in the art will recognize that the facility may employ any number of feature generators and any number of sets of physiological data (or portions thereof) in the generation of feature vectors. In some embodiments, the facility randomly selects a number of previously-generated feature generators for use in generating feature vectors rather than employing each and every available feature generator. In some embodiments, the facility creates and/or modifies feature generators by, for example, randomly generating expression trees, randomly assigning weights to connections within a neural network, and so on.

In some embodiments, after the facility generates a number of feature vectors, the facility employs some form of novelty search to identify the most "novel" feature vectors among the generated feature vectors. Novelty corresponds to how different a particular feature vector is from each of a comparison set of other feature vectors (made up of any feature vectors generated by the facility during a current iteration and feature vectors produced by feature generators selected in any earlier iteration); the greater the difference from the feature vectors of the comparison set, the greater the novelty. The facility uses a form of distance as a measure of novelty (i.e., how "far" each feature vector is from the other feature vectors). In this case, for each generated feature vector, the facility calculates the distance between that feature vector and each of the other generated feature vectors and performs an aggregation of the generated distance values, such as calculating an average or mean (e.g., arithmetic, geometric, harmonic, etc.) distance value for the feature vector, or a total (sum) distance between the feature vector and each of the other generated feature vectors, identifying a mode distance value, a median distance value, a maximum distance value for the feature vector, and so on. For example, using the feature vectors of Table 2 (for patients 1, 2, and n), the distances for each set of feature vectors could be calculated as such:

F1-F2 distance:

$$\sqrt{(-29.76-5.48)^2 + (-0.6-6.67)^2 + (4.3-185.74)^2} = 184.97.$$

F1-F3 distance:

$$\sqrt{(-29.76-905.83)^2 + (-0.6-9.57)^2 + (4.3-0.04)^2} = 936.23$$

F2-F3 distance:

$$\sqrt{(5.48-905.83)^2 + (6.67-9.57)^2 + (185.74-0.04)^2} = 919.70.$$

In this example, the total Euclidean distance between each of the feature vectors has been calculated as a means for calculating a difference between each of two vectors. In addition to the feature vectors generated by a current set (i.e., a current generation) of feature generators, the facility includes feature vectors produced by feature generators selected in an earlier generation. In some examples, the facility applies a weight, such as a randomly generated weight, to each of the feature vectors and/or normalizes each set of feature vectors prior to comparison. Thus, the distance measurements for each of the feature vectors in this example are as follows:

TABLE 3

| Feature Generator | Distance to F1 | Distance to F2 | Distance to F3 | Average Distance | MAX Distance |
|---|---|---|---|---|---|
| F1 | — | 184.97 | 936.23 | 560.60 | 936.23 |
| F2 | 184.97 | — | 919.70 | 552.34 | 919.70 |
| F3 | 936.23 | 919.70 | — | 927.97 | 936.23 |

In this example, the facility identifies the most "novel" feature vectors based on the calculated distances, which act as a "novelty score" or "fitness score" for each of the feature vectors. The facility identifies the feature vectors with the greatest average distance to other vectors (e.g., the feature vector generated by F3), the feature vectors with the greatest MAX distance (e.g., the feature vectors generated by F1 and F3), and so on. In some examples, the number of novel feature vectors identified is fixed (or capped) at a predetermined number, such as five, ten, 100, 500, etc. In other examples, the number of novel feature vectors to be identified is determined dynamically, such as the top 10% of analyzed feature vectors based on novelty scores, any feature vectors having a novelty scores that is more than a predetermined number of standard deviations beyond a mean novelty score for the analyzed feature vectors, and so on. The feature generators that produced each of these identified novel feature vectors can then be added to the set of features available for use as inputs to models constructed and evaluated by the machine learning pipeline. Those models can be applied to patient data for, e.g., diagnostic, predictive, therapeutic, or other analytic, scientific, health-related or other purposes.

In some embodiments, in addition to providing the feature generators used to generate the identified novel feature vectors for use by the machine learning process, the facility randomly mutates or modifies the feature generators used to generate the identified novel feature vectors. Each mutation effects some change in the corresponding feature generator and creates a new version of the feature generator that can be used to contribute to a new generation of feature generators. The facility uses this new feature generator to generate new feature vectors, and then assesses the novelty of the new feature vectors. Moreover, the corresponding feature generator can be further mutated to continue this process of feature vector and feature generation creation. For example, a feature generator expressed in the form of an equation, such as $F1_0=A+C-D$, can be mutated by randomly selecting one or more element(s) of the equation and replacing the selected element(s) with other elements (e.g., randomly selected elements). In this example, the equation can be changed by replacing A with B to create $F1_1=B+C-D$ or replacing C-D with $$\sqrt[3]{C-B^2}$$

to create $$F1_1 = B + \sqrt[3]{C-B^2}.$$

In this case, the subscripted 0 and 1 have been included to represent a generational marker or count for each of the feature generators. In other words, $F1_0$ represents F1 above (Eq 1) at generation 0 (i.e., the first generation), $F1_1$ represents a mutated version of F1 at generation 1 (i.e., the second generation), and so on. In some cases, an earlier generation (or a transformation thereof) is included as an element in subsequent generations, such as $F2_1=\sqrt{F2_0}+C^2$ or $F2n=\sqrt{F2_{n-1}}+C^2$ ($n\neq 0$).

In some embodiments, the facility obtains features in different ways. For example, the facility may receive from a user, such as a domain expert, a set of features (and corresponding feature generators) that the user has identified as being optimal and/or that the user desires to be tested. As another example, the features may be editorially selected from one or more feature stores. In some cases, features automatically generated by the facility can be combined with other features to create various hybrid features. Even features of unknown provenance may be used.

In some embodiments, the facility identifies genomes to train models, identifies, from among these genomes, the "best" (highest rated) genomes, and mutates the identified genomes to produce even more genomes that can be used to train models. After using a genome to train one or more models, the facility applies each trained model to a validation data set so that the trained model can be scored (e.g., how well does the trained model correctly identify and/or classify subjects in the underlying validation data set). The facility mutates the genomes that produce the best results (e.g., have the highest validation or fitness scores), trains new models using these mutated genomes, and repeats this process until one or more termination criteria are met (e.g., a predetermined number of generations, no additional high scoring (higher than a predetermined or dynamically generated threshold) genomes are generated during a predetermined or dynamically number (e.g., 1, 5, 8, 17, etc.) of previous generations, a combination thereof, etc.).

In some embodiments, the facility uses previously identified or generated genomes as a first set of genomes (i.e., a first generation) from which to discover genomes for machine learning algorithms. In other examples, the facility automatically generates a first generation of genomes by, for each genome, randomly (with or without replacement) selecting one or more feature vectors from one or more previously generated sets of feature vectors (e.g., a feature vector produced by applying a feature generator to a set of training data). A genome may also include one or more machine learning algorithm parameters to the machine learning algorithm, such as the number of predictors (e.g., regressors, classifiers, the number and/or the maximum number of decision trees to use for a machine learning algorithm, etc.) to use for an underlying ensemble method associated with the algorithm, a maximum depth for a machine learning algorithm (e.g., maximum depth for decision trees), and so on. In the event that the genome is configured to be used with one specific machine learning algorithm, the genome can be configured to define a value for each machine learning parameter associated with that machine learning algorithm. In other cases, one of the elements of the genome selects among different machine learning algorithms and may be mutated so that the genome and its corresponding parameter values are used with different machine learning algorithms to train models over the evolutionary process. For example, during a first generation, a genome may identify a machine learning algorithm that relies on decision trees while a mutated version of that same genome identifies a machine learning algorithm that uses one or more support vector machines, linear models, etc. In these cases, the genome may specify a modeling parameter for each and every machine learning algorithm that may be combined with the genome to train a model. Thus, a single genome may include machine learning parameters for multiple machine learning algorithms. However, a genome need not include each and every modeling parameter for a corresponding machine learning algorithm. In the event that a model is to be trained using a particular machine learning algorithm and a genome that does not include a value for a machine learning parameter of that machine learning algorithm, the facility can retrieve a default value for these parameters from, for example, a machine learning parameter store.

For example, a set of genomes may be represented as:

TABLE 4

| $G1_1$ | MLA = 4 | F23 | F78798 | F32 | F55 | F453 | F234 | |
|---|---|---|---|---|---|---|---|---|
| $G2_1$ | MLA = 9 | F9701 | F223 | F1 | F63 | F349 | P9:1 = 7 | |
| $G3_1$ | MLA = 2 | F823 | F525 | F732 | F525 | F125 | | |
| $G4_1$ | MLA = 6 | F597 | F135 | F404 | F31 | P6:1 = 5 | P6:2 = 150 | |
| ... | | | | | | | | |
| $G20_1$ | MLA = 1 | F43 | F65 | P1:1 = 8 | P1:2 = 218 | P1:3 = 0.3 | | | where each row corresponds to a different genome (named in the first column from the left) from among a first generation of selected or generated genomes and identifies a machine learning algorithm ("MLA"; second column from the left) to use to train a model using the genome, such as an index into a machine learning algorithm store. For example, genome $G3_1$ specifies a machine learning algorithm corresponding to index 2 in a machine learning algorithm store (MLA=2). In this example, each non-bolded region (to the right of the second column) identifies a different feature. A genome can also include a corresponding feature generator or a reference to the corresponding feature generator, such as a link to feature generator store. As discussed above, these features may be generated automatically by the facility and/or retrieved from another source.

Furthermore, each bolded region in Table 4 represents a value for a particular machine learning parameter. In this example set of genomes, machine learning parameters are represented by an indicator or reference (e.g., P6:1) followed by an equals sign and a corresponding value. For example, machine learning algorithm parameter P6:1 has a corresponding value of 8 in genome $G20_1$. In this example set of genomes, each machine learning parameter is presented as an index into a two-dimensional array, such that "P6:1" represents the "first" machine learning parameter of the "sixth" machine learning algorithm (i.e., the machine learning parameter with an index of 1 for the machine learning algorithm with an index of 6). As discussed above, a genome may specify values for any or all machine learning parameters that may be used to training a model using the genome (or a mutated version of that genome). Moreover, as is clear from Table 4, genomes may be of varying length. For example, genome $G1_1$ includes values for six features and zero machine learning parameters while gnome $G2_1$ includes values for two features and three machine learning parameters. Accordingly, the facility may employ variable-length genomes in the machine learning processes.

In some embodiments, the facility may filter features from within genomes and/or filters genomes themselves to avoid redundancy among each. In order to filter features and/or genomes, the facility generates correlation values for each pair and discards one item of the pair. To identify and filter correlated features from a genome, the facility generates, for each of the features, a feature vector by applying a feature generator associated with the feature to a training set of data to produce a set of values. The facility compares each of the generated feature vectors to the other generated feature vectors to determine whether any of the feature vectors are "highly" correlated (i.e., not "novel" within the selected set of feature vectors). For example, the component may calculate a distance value for each of the generated feature vectors relative to the other feature vectors (as discussed above with respect to identifying novel feature generators) and, if the distance between any pair (set of two) is less than or equal to a distance threshold (i.e., "highly" correlated or not "novel"), discard a feature corresponding to one of the pair of feature vectors. Moreover, the facility may replace the discarded feature with a new feature, such as a randomly-selected feature. Similarly, the facility may identify and discard redundant genomes by generating, for each feature of the genome, a feature vector, calculating distance metrics for each pair (set of two) of genomes based on the generated feature vectors, and identifying pairs of genomes whose calculated distances do not exceed a genome distance threshold. For each identified pair of genomes, the facility may discard or mutate one or both of the genomes to reduce correlation and redundancy among a group of genomes. Although distance is used in this example as a metric for determining a correlation between two vectors or sets of vectors, one of ordinary skill in the art will recognize that correlations between two or sets of vectors can be calculated in other ways, such as normalized cross-correlation, and so on. In some embodiments, the facility may employ additional or other techniques to filter genomes, such as generating a graph where features represent vertices in the graph which are connected via edges in the graph. An edge between two features is generated if, for example, a correlation value between the two features exceeds a predetermined correlation threshold and/or the distance between the two features is less than a predetermined distance threshold. Once the graph is generated, the facility removes connected vertices (features) from the graph until no edges remain in the graph (an edge being removed when a connected vertex is removed) and selects the remaining non-connected vertices (features) for inclusion in the "filtered" genome. In some cases, the facility may randomly select connected vertices for removal. Moreover, the facility may perform this process multiple times for a set of vertices (features) and then select a preferred "filtered" genome, such as the genome with the most or least vertices (features) removed.

In order to test the fitness or validity of each genome, the facility trains at least one model using the features, machine learning parameters, and/or machine learning algorithm(s) of that genome. For example, the facility can use AdaBoost ("Adaptive Boosting") techniques to train a model using the corresponding features, machine learning parameters, machine learning algorithm, and a training set of data. However, one of ordinary skill in the art will recognize that many different techniques can be used to train one or more models given a genome or a set of genomes. After the model is trained, the facility applies the trained model to one or more sets of validation data to assess how well the trained model identifies and/or classifies previously-identified or classified subjects within the validation data set. For example, a genome may be generated to train models to identify patients represented in a data set who are likely to have diabetes. Once a model is trained using one of these genomes, the trained model can be applied to a validation set of data to determine a validation score that reflects how well the trained model identifies patients from the validation set that are known to have or now have diabetes; scoring (adding) one "point" for every correct determination (e.g. true positives and true negatives) and losing (subtracting) one "point" for every incorrect determination (e.g., false positives and false negatives). Thus, an overall score for the trained model can be determined based on how many "points" the trained model scores when applied to one or more sets of validation data. One of ordinary skill in the art will recognize that several techniques may be used to generate a fitness score for a trained model, such as calculating the area under a corresponding receiver operating characteristic (ROC) curve, calculating a mean squared prediction error, f scores, sensitivity, specificity, negative and positive predictive values, diagnostic odds ratios, and so on. In this example, where a single machine learning algorithm is trained using the genome, the generated fitness score may be similarly attributed to the genome. In other case, the genome may be used to train multiple machine learning algorithms and each of those trained machine learning algorithms may be applied to multiple validation sets to produce, for each genome used to train machine algorithms, multiple fitness scores. In these cases, the facility generates a fitness score for the corresponding genome by aggregating each of the fitness scores generated for the machine learning algorithms trained using the genome. In some cases, the generated fitness scores may be aggregated and/or filtered prior to aggregation.

In some embodiments, after the facility has produced fitness scores for each of the genomes, the facility identifies the "best" genomes based on these fitness scores. For example, the facility can establish a fitness threshold based on the produced fitness scores and identify the "best" genomes as those genomes whose resulting fitness scores exceed the fitness threshold. The fitness threshold may be generated or determined in any number of ways, such as receiving a fitness threshold from a user, calculating a fitness threshold based on the set of fitness scores (e.g., average, average plus 15%, top fifteen, top n-th percentile (where n is provided by a user or generated automatically by the facility), and so on. The facility then stores each of the genomes in association with their corresponding fitness scores and selects the genomes identified as "best" for mutation (i.e., the genomes having a fitness score that exceeds a fitness threshold).

In some embodiments, the facility mutates a genome by adding, removing, or changing any one or more of the feature vectors or machine learning parameters of the genome. For example, Table 5 below represents a number of mutations to the genomes represented above in Table 4.

example, based on its low fitness score, the facility did not select genome $G3_1$ for mutation and, therefore, Table 5 does not include a corresponding entry for a mutated version of this genome. Moreover, genome $G1_1$ has been mutated (represented as $G1_2$) by removing three feature vectors (represented with a strikethrough) and changing the references machine learning algorithm index from 4 to 5. Furthermore, the facility has mutated genome $G2_1$ by 1) removing feature vector F9701, 2) adding feature vector F584, and 3) adjusting machine learning parameter $P9_1$ from 7 to 12; genome $G4_1$ by adding features F24 and F982; and genome $Gn_1$ by multiplying values generated by F65 by values generated by F14. These mutated genomes can then be used to train one or more machine learning algorithms, scored by applying the trained machine learning algorithm to one or more validation data sets, selected for mutation, mutated, and so on. The facility performs this process until a termination point is reached, such as when a predetermined number of generations has been produced (e.g., six, 30, 100,000, etc.), and so on.

FIG. 1 is a block diagram illustrating an environment 100 in which the facility operates in accordance with some embodiments of the disclosed technology. In this example, environment 100 includes service provider 110, signal recorder 140 (e.g., a wide-band biopotential measuring equipment), data providers 150, patient 160, and network 160. In this example, service provider includes facility 120, which includes discover features component 121, process component 122, apply feature generators component 123, identify novel feature vectors component 124, discover genomes component 125, spawn genome component 126, identify high-performing genomes component 127, patient data store 130, model store 131, feature vector store 132, and feature generator store 133. Discover features component 121 is invoked by the facility to identify and mutate feature generators based on received data. Process component 122 is invoked by the discover features component 121 to process and transform patient signal data, such as raw signal data from signal recorder 140 (e.g., one or more measurement devices and/or systems used to collect the underlying data such as wide-band biopotential measuring equipment, etc.), 3-D image data, etc. Apply feature generators component 123 is invoked by the discover features component to apply a set of one or more feature generators to the processed and transformed patient signal data. Identify novel feature vectors component 124 is invoked by the discover features component to identify the most novel feature vectors from among a group of feature vectors generated by, for example, one or more feature generators. Discover genomes component 125 is invoked by the facility 120 to generate, analyze, and mutate genomes for use by machine learning algorithms. Spawn genome component 126 is invoked by the discover genomes component to generate a genome comprising any number of feature vectors and/or machine learning parameters. Identify high-performing genomes

TABLE 5

| $G1_2$ | MLA = 5 | F23 | F78798 | F32 | ~~F55~~ | ~~F453~~ | ~~F234~~ | | |
|---|---|---|---|---|---|---|---|---|---|
| $G2_2$ | MLA = 9 | ~~F9701~~ | F223 | F1 | F63 | F349 | F584 | $P9:1 = 12$ | |
| $G4_2$ | MLA = 6 | F597 | F135 | F404 | F31 | F24 | F982 | $P6:1 = 5$ | $P6:2 = 150$ |
| | | | | . . . | | | | | |
| $G20_2$ | MLA = 1 | F43 | F65*F14 | $P1:1 = 8$ | $P1:2 = 218$ | $P1:3 = 0.3$ | | | |

In this example, each row corresponds to a different genome (named in the first column from the left) from among a second generation of genomes selected for mutation. In this component 127 is invoked by the discover genomes component to identify, from among a group of genomes, the genomes that have a corresponding fitness score that exceeds a fitness threshold. Patient data store 130 includes physiological patient data, such as raw physiological data (including but not limited to data obtained via, e.g., signal recorder 140), transformed physiological data, biographical information, demographic information, etc. These data may be stored anonymously to protect the privacy of each of the corresponding patients and may be processed and encrypted to ensure that its transmission and storage complies with any governing laws and their implementing regulations, such as the U.S. Health Insurance Portability and Accountability Act of 1996 (as amended), the European Data Protection Directive, the Canadian Personal Information Protection and Electronics Documents Act, the Australian Privacy Act of 1988, Japan's Personal Information Protection Act of 2015 (as amended), state and provincial laws and regulations, and so on. Model store 131 stores information about models generated by applying machine learning techniques to training data, such as the machine learning techniques described in Christopher M. Bishop, *Pattern Recognition and Machine Learning* (2006) (Library of Congress Control Number: 2006922522; ISBN-10: 0-387-31073-8), which is herein incorporated by reference in its entirety. Feature vector store 132 stores sets of feature vectors generated by applying one or more feature generators to a set of physiological data. Feature generator store 133 stores sets of feature generators that can be applied to patient physiological data and can include multiple generations of feature generators. Genome store 134 stores generated and/or mutated genomes created by the facility and/or other sources. Machine learning parameters store 135 stores, for each of a number of machine learning algorithms, a set of parameters that can serve as inputs to that machine learning algorithm and additional information related to the parameter, such as a maximum value for a corresponding parameter, a minimum value for a corresponding parameter, a default value for a corresponding parameter, etc. Machine learning algorithm store 133 stores the logic for each of a number of machine learning algorithms, each of which can be selectively trained and validated by the facility. In this example, a signal recorder 140 is connected to patient 160 via electrodes 145 and includes facility 120, one or more output devices 142, such as a monitor, printer, speaker, etc., and one or more input devices 144, such as settings controls, keyboard, biometric data reader, etc. Thus, as in this example, the facility can be configured to operate remotely from a patient and other diagnostics equipment and/or in conjunction with or part of the diagnostics equipment such as a wide-band biopotential measuring equipment (i.e., any device configured to capture unfiltered electrophysiological signals, including those with spectral components that are not altered). Accordingly, the facility can be configured to operate in real-time with the reading of physiological data and/or can be applied to previously recorded physiological data. Data providers 150, each of which includes a data store 152, can provide information for analysis or use by the facility such as, physiological patient data recorded off-site (e.g., at a hospital or clinic without access to a facility on premises, third-party data providers, etc.), feature vectors and/or feature generators produced or generated elsewhere, and so on. Network 170 represents communications links over which the various elements of environment 100 may communicate, such as the internet, a local area network, and so on.

In various examples, these computer systems and other devices can include server computer systems, desktop computer systems, laptop computer systems, netbooks, tablets, mobile phones, personal digital assistants, televisions, cameras, automobile computers, electronic media players, appliances, wearable devices, other hardware, and/or the like. In some embodiments, the facility 120 may operate on specific-purpose computing systems, such as wide-band biopotential measuring equipment (or any device configured to capture unfiltered electrophysiological signals, including electrophysiological signals with unaltered spectral components), electroencephalogram equipment, radiology equipment, sound recording equipment, and so on. In various examples, the computer systems and devices include one or more of each of the following: a central processing unit ("CPU") configured to execute computer programs; a computer memory configured to store programs and data while they are being used, including a multithreaded program being tested, a debugger, the facility, an operating system including a kernel, and device drivers; a persistent storage device, such as a hard drive or flash drive configured to persistently store programs and data (e.g., firmware and the like); a computer-readable storage media drive, such as a floppy, flash, CD-ROM, or DVD drive, configured to read programs and data stored on a computer-readable storage medium, such as a floppy disk, flash memory device, CD-ROM, or DVD; and a network connection configured to connect the computer system to other computer systems to send and/or receive data, such as via the internet, a Local Area Network (LAN), a Wide Area Network (WAN), a point-to-point dial-up connection, a cell phone network, or another network and its networking hardware in various examples including routers, switches, and various types of transmitters, receivers, or computer-readable transmission media. While computer systems configured as described above may be used to support the operation of the facility, those skilled in the art will readily appreciate that the facility may be implemented using devices of various types and configurations, and having various components. Elements of the facility may be described in the general context of computer-executable instructions, such as program modules, executed by one or more computers or other devices. Generally, program modules include routines, programs, objects, components, data structures, and/or the like configured to perform particular tasks or implement particular abstract data types and may be encrypted. Furthermore, the functionality of the program modules may be combined or distributed as desired in various examples. Moreover, display pages may be implemented in any of various ways, such as in C++ or as web pages in XML (Extensible Markup Language), HTML (HyperText Markup Language), JavaScript, AJAX (Asynchronous JavaScript and XML) techniques, or any other scripts or methods of creating displayable data, such as the Wireless Access Protocol (WAP). Typically, the functionality of the program modules may be combined or distributed as desired in various embodiments, including cloud-based implementations, web applications, mobile applications for mobile devices, and so on.

The following discussion provides a brief, general description of a suitable computing environment in which the disclosed technology can be implemented. Although not required, aspects of the disclosed technology are described in the general context of computer-executable instructions, such as routines executed by a general-purpose data processing device, e.g., a server computer, wireless device, or personal computer. Those skilled in the relevant art will appreciate that aspects of the disclosed technology can be practiced with other communications, data processing, or computer system configurations, including: internet or otherwise network-capable appliances, hand-held devices (including personal digital assistants (PDAs)), wearable computers (e.g., fitness-oriented wearable computing devices), all manner of cellular or mobile phones (including Voice over IP (VoIP) phones), dumb terminals, media players, gaming devices, multi-processor systems, microprocessor-based or programmable consumer electronics, set-top boxes, network PCs, mini-computers, mainframe computers, and the like. Indeed, the terms "computer," "server," "host," "host system," and the like are generally used interchangeably herein, and refer to any of the above devices and systems, as well as any data processor.

Aspects of the disclosed technology can be embodied in a special purpose computer or data processor, such as application-specific integrated circuits (ASIC), field-programmable gate arrays (FPGA), graphics processing units (GPU), many core processors, and so on, that is specifically programmed, configured, or constructed to perform one or more of the computer-executable instructions explained in detail herein. While aspects of the disclosed technology, such as certain functions, are described as being performed exclusively on a single device, the disclosed technology can also be practiced in distributed computing environments where functions or modules are shared among disparate processing devices, which are linked through a communications network such as a Local Area Network (LAN), Wide Area Network (WAN), or the internet. In a distributed computing environment, program modules may be located in both local and remote memory storage devices.

Aspects of the disclosed technology may be stored or distributed on tangible computer-readable media, including magnetically or optically readable computer discs, hard-wired or preprogrammed chips (e.g., EEPROM semiconductor chips), nanotechnology memory, biological memory, or other computer-readable storage media. Alternatively, computer-implemented instructions, data structures, screen displays, and other data under aspects of the disclosed technology may be distributed over the internet or over other networks (including wireless networks), on a propagated signal on a propagation medium (e.g., electromagnetic wave(s), sound wave, etc.) over a period of time, or they may be provided on any analog or digital network (packet switched, circuit switched, or other scheme). Furthermore, the term computer-readable storage medium does not encompass signals (e.g., propagating signals) or transitory media.

Figure 2:
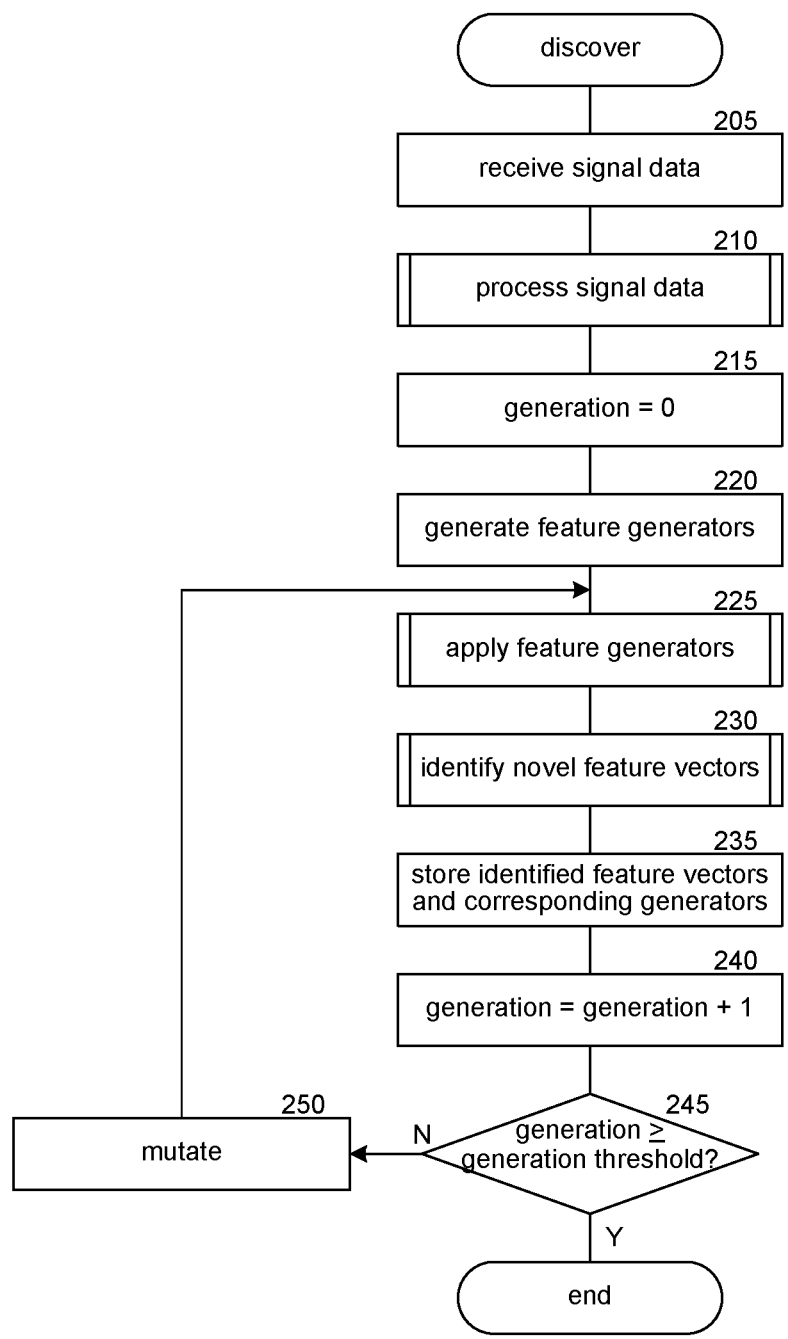
FIG. 2 is a flow diagram illustrating the processing of a discover features component in some embodiments.

FIG. 2 is a flow diagram illustrating the processing of a discover features component 121 in accordance with some embodiments of the disclosed technology. The discover features component is invoked by the facility to identify novel feature vectors based on selected patient data. In block 205, the component receives physiological signal data, such as raw signal data received directly from signal recorder, previously-generated physiological signal from another device or site, etc. Several techniques exist for collecting and analyzing physiological signals (e.g., electrophysiological signals, biosignals) from patients for diagnostic and other purposes including, for example, activity trackers, echocardiograms, wide-band biopotential measuring equipment, electroencephalograms, electromyograms, electrooculography, galvanic skin response, heart rate monitors, magnetic resonance imaging, magnetoencephalograms, mechanomyograms, wearable technology devices (e.g., FIT-BITs), and so on. While data provided by these systems can be helpful in identifying medical concerns and diagnosing medical conditions, they are often only a starting point for the diagnosis process. Moreover, given the specific nature of most of these systems, the data they analyze is often over-filtered to reduce complexity for the system itself or for, e.g., a technician, physician, or other health care provider (in such cases, to reduce visual complexity, etc.) thereby eliminating data that potentially have untapped diagnostic value. In block 210, the component invokes a process signal data component to process and transform the received signal data, which can produce multiple sets of data and transformed data. In block 215, the component sets a generation value equal to 0. In block 220, the component generates one or more feature generators by, for example, randomly generating an expression tree, randomly generating a set of weights for a neural network, randomly mutating one or more of a set of previously-generated feature generators, and so on. In block 225, the component invokes an apply feature generators component to apply the generated feature generators to one or more sets of the processed signal data to produce a set of feature vectors. In block 230, the component invokes an identify novel feature vectors component to identify the most novel feature vectors from among the group of feature vectors generated by the feature generators. In block 235, the component stores the feature generators that produced the identified feature vectors in, for example, a feature generator store. In block 240, the component increments the generation variable. In decision block 245, if the generation variable is greater than or equal to a generation threshold, then the component completes, else the component continues at block 250. The component may also use other stopping conditions, such as a number of generations of feature generators that do not produce at least a threshold number of novel feature vectors. In block 250, the component copies and mutates the identified feature generators and then loops back to block 225 to apply the mutated feature generators to one or more sets of the processed signal data. As discussed above, the component may apply any type or types of mutations to a feature generator, such as applying multiple point mutations and/or a random recombination to one or more expression trees, randomly generating a set of connection weights for a neural network, and so on.

Figure 3:
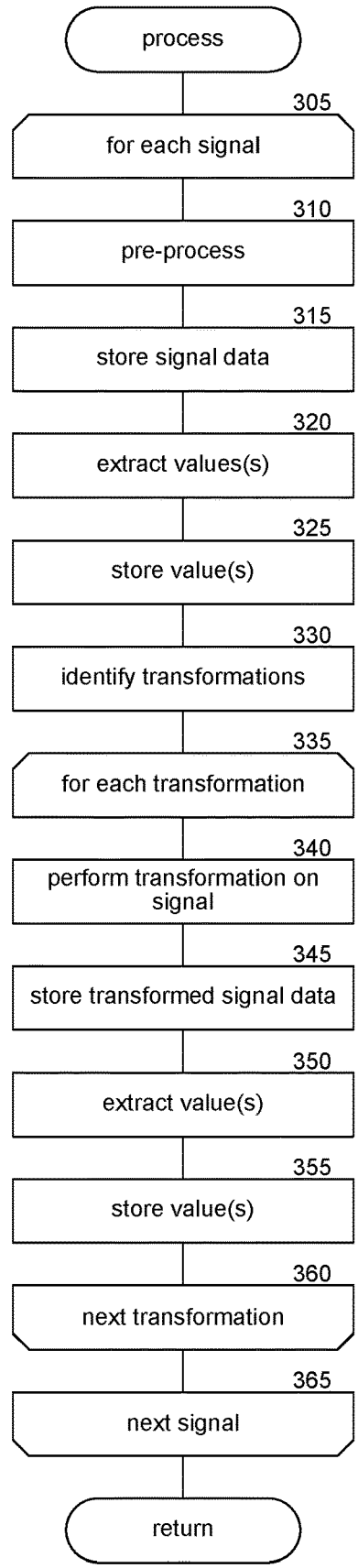
FIG. 3 is a flow diagram illustrating the processing of a process component in some embodiments.

FIG. 3 is a flow diagram illustrating the processing of a process component 122 in accordance with some embodiments of the disclosed technology. The process component is invoked by the discover features component to process and transform patient signal data. In blocks 305 through 365, the component loops through each signal (or data set) of a set of received signals (or set of data sets), each signal representing physiological data received from a patient. In block 310, the component pre-processes the received signal, such as applying one or more signal filters to the signal, performing a peak search on the data and discarding extraneous information, down-sampling the received signal, up-sampling the received signal, sub-sampling the received signal, converting an analog signal to a digital signal, converting image data to signal data, and so on. In block 315, the component stores the pre-processed signal in, for example, a patient data store. The signal data may be stored anonymously (i.e., without explicitly or implicitly identifying the corresponding patient, etc.). However, different instances of signal data associated with the same patient may be associated with an anonymized unique identifier so that multiple signals from a single patient can be used in conjunction for training and diagnostic purposes. In block 320, the component extracts one or more values from the stored signal data. In block 325, the component stores the one or more extracted values. In block 330, the component identifies any transformations to be applied to the signal. For example, the facility may store an indication of a set of transformations or transformation functions (e.g., Fourier transforms, functions to apply to the signal, derivatives, partial derivatives, and so on) to apply to a particular signal. As another example, the facility may randomly select, from among a catalog of transformations, one or more transformations to apply to the signal data. In blocks 335 through 360, the component loops through each of the transformations and applies the transformation to the signal. In block 340, the component applies the transformation to the signal (e.g., calculating the third derivative with respect to a particular variable, calculating the result of a composite function generated by applying one function to the signal data (i.e., a function representative of the signal data), etc.). In block 345, the component stores the transformed signal data in, for example, a patient data store. In block 350, the component extracts one or more values from the transformed signal data. In block 355, the component stores the one or more extracted values. In block 360, if there are any identified transformations yet to be applied, then the component selects the next transformation and loops back to block 335 to apply the transformation to the signal data, else the component continues at block 365. In block 365, if there are any signals yet to be analyzed, then the component selects the next signal and loops back to block 305 to process the next signal, else the component completes.

Figure 4:
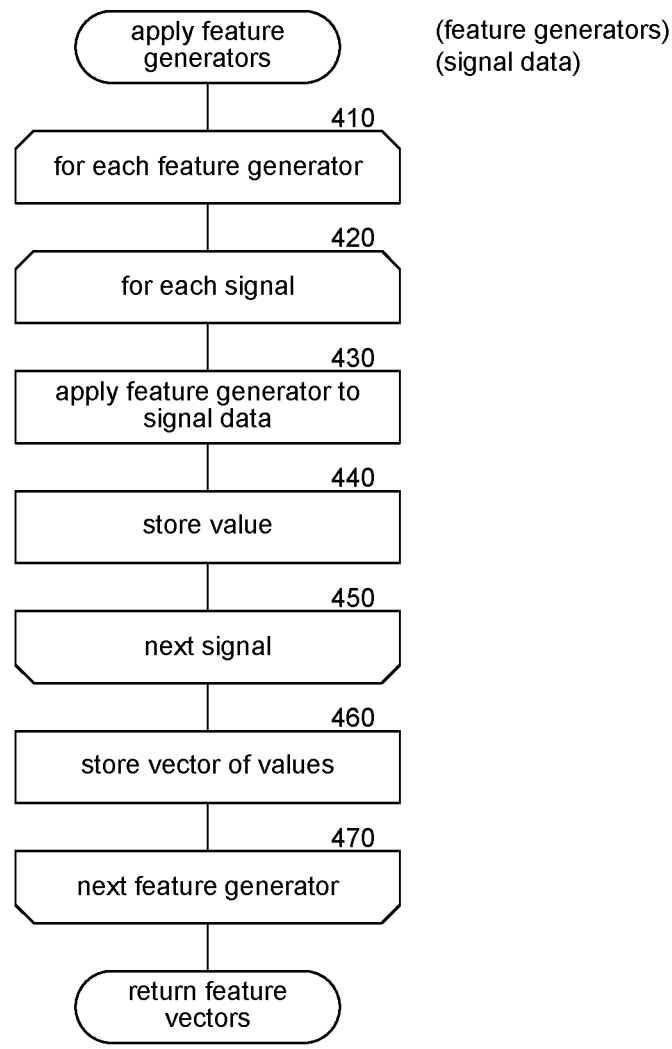
FIG. 4 is a flow diagram illustrating the processing of an apply feature generators component in some embodiments.

FIG. 4 is a flow diagram illustrating the processing of an apply feature generators component 123 in accordance with some embodiments of the disclosed technology. The apply feature generators component is invoked by the discover features component 121 to apply a set of one or more feature generators to signal data, such as pre-processed and transformed signal data, modeled signal data, etc. In blocks 410 through 470, the component loops through each of a received set of feature generators and applies the feature generator to each signal in a received set of signal data. For example, the received signal data can include multiple sets of signal data for each of multiple patients, multiple transformations of that data, and so on. In blocks 420 through 450, the component loops through each of the signals to apply the feature generators to the signal data. In block 430, the component applies the currently-selected feature generator to the currently-selected signal data. For example, the component may apply the feature generator to each of a pre-processed version of the currently-selected data signal and any transformed version of that data. As another example, the component "plugs in" or substitutes coefficients generated by modeled signal data into a feature generator with a set of variables to produce an output feature value. As another example, the component can apply one or more elements of modeled signal data to a neural network to produce an output feature value. In block 440, the component stores the output value. In block 450, if there are any signals yet to be analyzed, then the component selects the next signal and loops back to block 420 to process the next signal, else the component continues at block 460. In block 460, the component generates a feature vector that includes each of the generated feature values and stores the feature vector in association with the feature generator in, for example, a feature vector store. For example, the feature vector may comprise an array of features and a link to, or identifier of, the corresponding feature generator. The component may also associate the feature vector with the signal data used to generate the feature vector. In block 470, if there are any feature generators yet to be processed, then the component selects the next feature generator and loops back to block 410 to process the feature generator, else the component completes.

Figure 5:
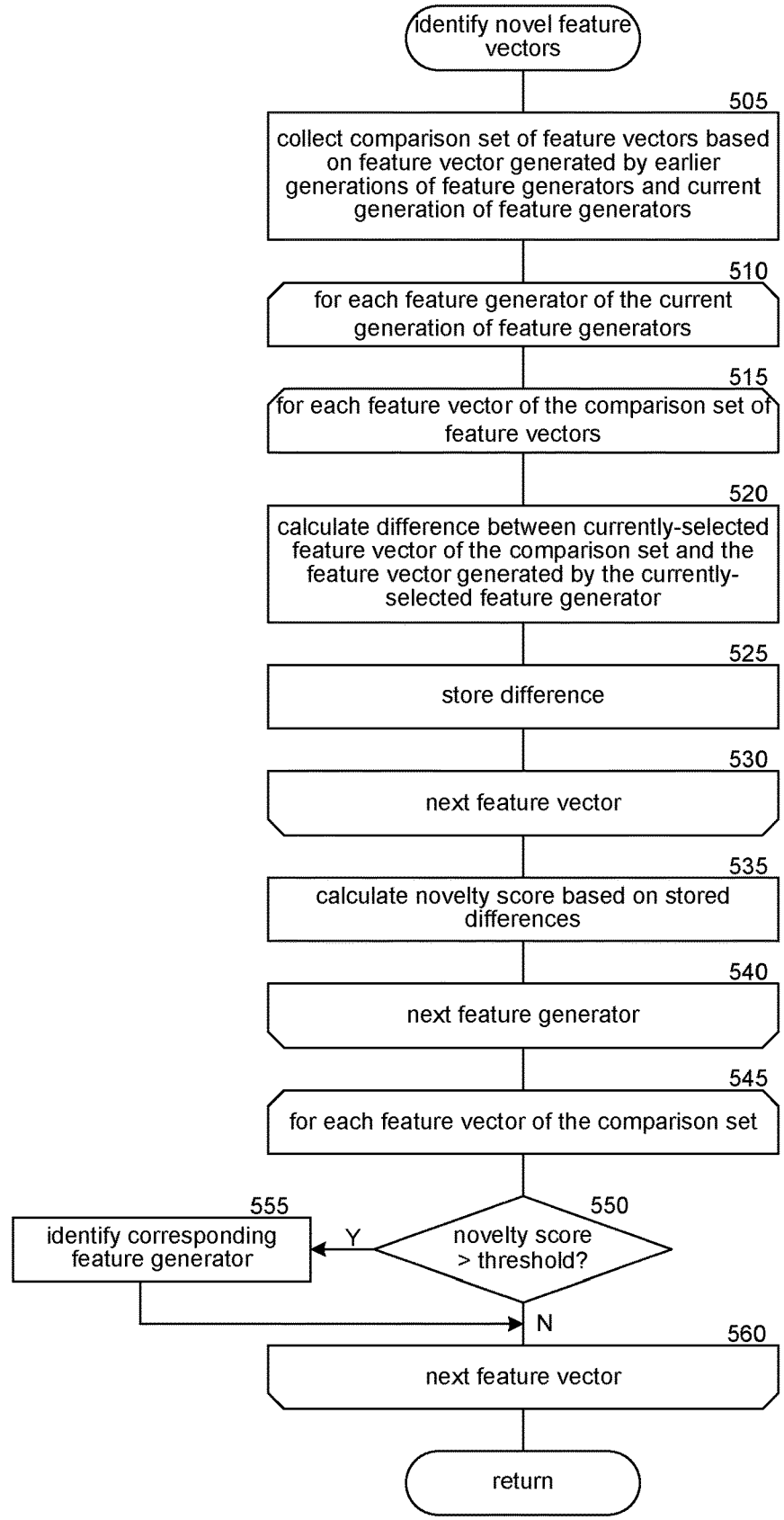
FIG. 5 is a flow diagram illustrating the processing of an identify novel feature vectors component in some embodiments.

FIG. 5 is a flow diagram illustrating the processing of an identify novel feature vectors component 124 in accordance with some embodiments of the disclosed technology. In this example, the facility receives a set of feature vectors and, for each feature vector, information related to the corresponding feature generator, such as an identifier for the feature generator. In block 505, the component collects a comparison set of feature vectors that includes, for example, feature vectors generated by feature generators of earlier generations that were found to be novel and the feature vectors generated by a current generation of feature vectors. For example, the component can randomly select a set of novel feature vectors from a feature store. In some cases, a request to retrieve feature vectors includes upper and lower limits on the number of features values for each feature vector to be retrieved, such as no less than 50 (lower threshold) and no more than 5000 (upper threshold). In blocks 510 through 540, the component loops through each feature vector of a current generation of feature generators to determine how different each of their corresponding feature vectors is to each of the feature vectors of the comparison set of feature vectors. In blocks 515 through 530, the component loops through each feature vector of the comparison set of feature vectors to compare each feature vector to the feature vector of the currently-selected feature generator. In block 520, the component calculates a difference value between the currently-selected feature vector of the comparison set and the feature vector of the currently-selected feature generator. For example, the component can calculate a distance value between each of the feature vectors. In block 525, the component stores the calculated difference value. In block 530, if there are any feature vectors yet to be compared, then the component selects the next feature vector and loops back to block 515 to process the feature vector, else the component continues at block 535. In block 535, the component calculates a novelty score for the currently-selected feature generator based on the stored difference values, such as an average or maximum distance, and stores the novelty score in association with the feature generator (e.g., in a feature generator store). In block 540, if there are any feature generators yet to be assessed, then the component selects the next feature generator and loops back to block 515 to process the feature generator, else the component continues at block 545. In blocks 545 through 560, the component tests whether each of the feature vectors is novel, based on the calculated novelty scores, and identifies any corresponding feature generators. In decision block 550, if the novelty score for the currently-selected feature generator is greater than a novelty threshold, then the component continues at block 555, else the component continues at block 560. The novelty threshold may be generated or determined in any number of ways, such as receiving a novelty threshold from a user, calculating a novelty threshold based on the set of novelty scores (e.g., average, average plus 25%, top n (where n is provided by a user or generated automatically by the facility), top tenth percentile), and so on. In this manner, the novelty threshold may change dynamically (e.g., from generation to generation) based on, for example, the number of generations without a new feature generator that exceeds the current novelty threshold to ensure that the facility is producing and testing new feature generators and corresponding features. In block 555, the component identifies the currently-selected feature vector as novel. In block 560, if there are any feature vectors yet to be processed, then the component selects the next feature vector and loops back to block 545 to process the feature vector, else the component completes.

Figure 6:
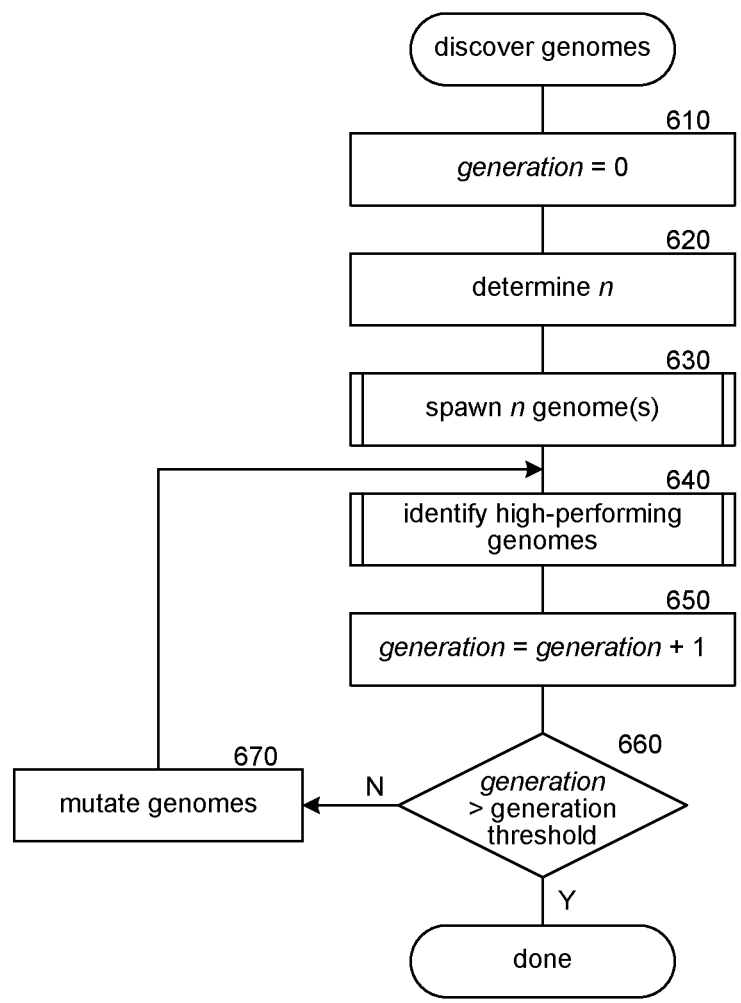
FIG. 6 is a flow diagram illustrating the processing of a discover genomes component in accordance with some embodiments.

FIG. 6 is a flow diagram illustrating the processing of a discover genomes component 126 in accordance with some embodiments of the disclosed technology. The facility invokes the discover genomes component to generate and analyze genomes for use by machine learning algorithms. In block 610, the facility initializes a generation variable equal to 0. In block 620, the component determines a number (n) of genomes to generate based on, for example, user input, system parameters, or randomly. In block 630, the component invokes a spawn genome component n time(s) to spawn the appropriate number of genomes. In block 640, the component invokes an identify high-performing genomes component to identify, from among the spawned genomes, the genomes that have a fitness score that exceeds a fitness threshold. In block 650, the component increments the generation variable. In decision block 660, if the generation variable is greater than or equal to a generation threshold, then processing of the component completes, else the component continues at block 670. In block 670, the component mutates the high-performing genomes and then loops back to block 640 to identify high-performing genomes from among the mutated genomes (e.g., the mutated genomes having fitness scores that exceed a fitness threshold). The component may mutate the genome by adding, changing, or removing (or any combination thereof) one or more elements of the variable-length genome. For example, the component may mutate one genome by replacing one feature with another feature and adding a new feature to the mutated genome. In another example, the component may select a new machine learning algorithm to associate with the genome. In this case, the component may also remove or mutate any irrelevant machine learning algorithm parameters and/or replace them with machine learning parameter values for the newly selected machine learning algorithm. As another example, genomes may use sexual reproduction techniques as a form of mutation by randomly selecting elements of multiple genomes and combining those elements to form a new genome. Moreover, one or more elements of a genome may be configured so that they remain fixed (i.e., are not changed) during the evolutionary process described herein.

Figure 7:
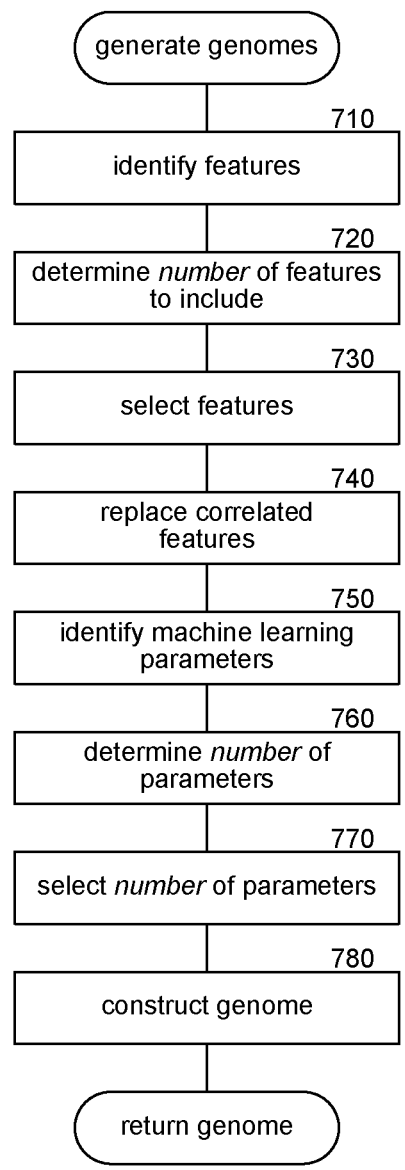
FIG. 7 is a flow diagram illustrating the processing of a spawn genome component in accordance with some embodiments.

FIG. 7 is a flow diagram illustrating the processing of a spawn genome component 126 in accordance with some embodiments of the disclosed technology. The discover genomes component 125 invokes the spawn genome component to generate a genome identifying any number of features, machine learning parameters, and/or machine learning algorithms. In block 710, the component identifies a set of available features, such as features referenced in one or more feature generator stores. In block 720, the component determines the number of features to include in the genome to be generated. For example, the component may determine the number of features to include in the genome to be generated based on user input, system parameters, or randomly. In block 730, the component randomly selects, from among the identified features, the determined number of features. In block 740, the component replaces correlated features from among the selected features with randomly selected features. In block 750, the component identifies a set of available machine learning parameters. For example, the component may identify, for each machine learning algorithm available to the facility, a set of parameters associated with that machine learning algorithm, which may be stored in a list or other data structure available to the component (e.g., a machine learning parameter store). In some cases, a genome may be generated for a single machine learning algorithm (or fixed set of machine learning algorithms). In this case, the component may identify only those machine learning parameters (or a proper subset thereof) that are associated with the single or fixed set of machine learning algorithms. In other cases, a genome may include an element that identifies a machine learning algorithm and that can be mutated. In this case, the component may identify any or all machine learning parameters of machine learning algorithms that are within the scope of this mutation (i.e., the parameters of the machine learning algorithms that the genome and its descendants may be associated with to train models during the evolutionary process described herein). In block 760, the component determines the number of machine learning parameters to include in the genome to be generated. For example, the component may determine the number of machine learning parameters to include in the genome to be generated based on user input, system parameters, or randomly. For example, one genome may include each and every machine learning parameter associated with a particular machine learning algorithm or a set of machine learning algorithms while another genome includes only a proper subset of machine learning parameters associated with a particular machine learning algorithm. In block 770, the component randomly selects, from among the identified machine learning parameters, the determined number of machine learning parameters and assigns a value to the parameter based on any associated constraints, such as randomly selecting a value between a minimum value and a maximum value associated with the parameter. In block 780, the component stores each of the selected features and machine learning parameters in a genome data structure and then returns the genome data structure.

Figure 8:
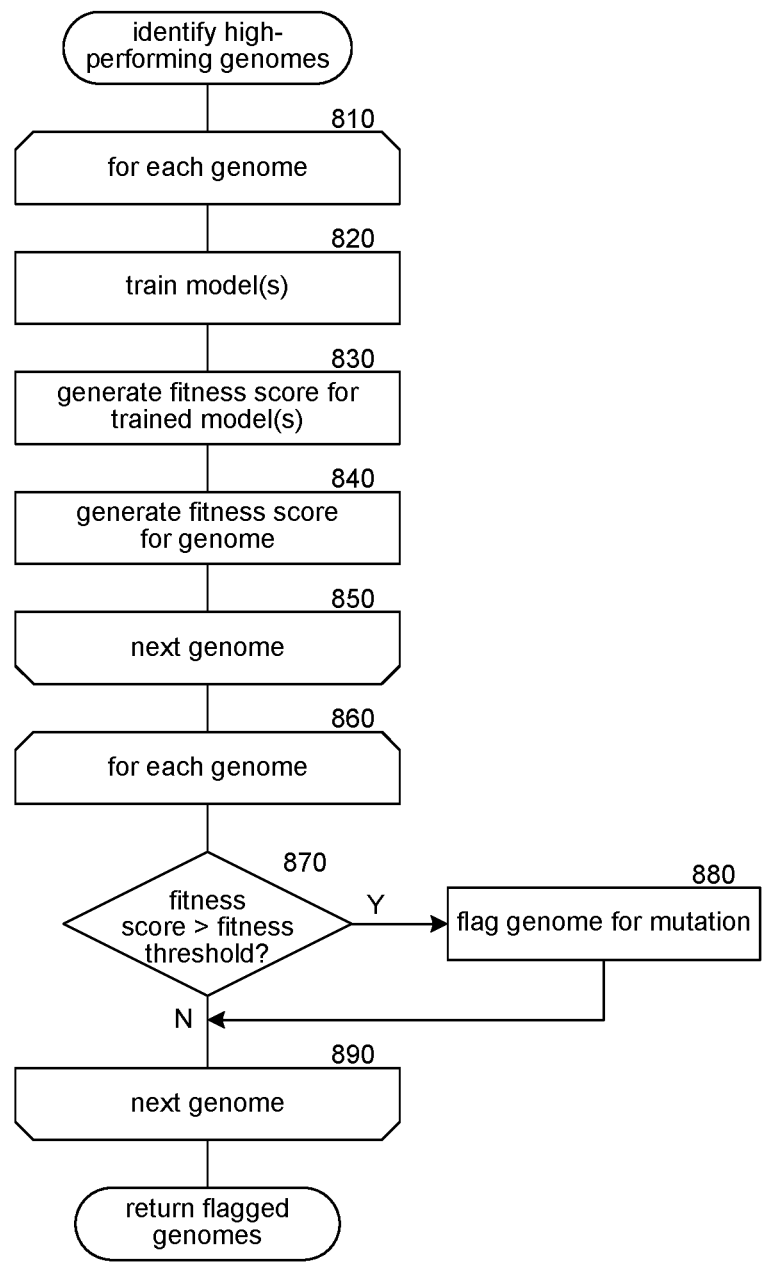
FIG. 8 is a flow diagram illustrating the processing of an identify high-performing genomes component in accordance with some embodiments.

FIG. 8 is a flow diagram illustrating the processing of an identify high-performing genomes component 127 in accordance with some embodiments of the disclosed technology. The discover genomes component invokes the identify high-performing genomes component to identify, from among a group of genomes, the genomes that have a corresponding fitness score that exceeds a fitness threshold (i.e., the genomes that are "high-performing"). In blocks 810 through 850, the component loops through a set of genomes provided to the component, such a first generation set of genomes, a mutated set of genomes, or some combination thereof. In block 820, the component trains one or more models using the currently-selected genome, including its features, machine learning parameters, and any specified machine learning algorithm. In the event that a machine learning parameter of the genome is not associated with the machine learning algorithm used to train the model, that machine learning parameter may be ignored. Similarly, if a particular machine learning algorithm requires as input a particular machine learning parameter that is not included in the currently-selected genome, the facility (or the machine learning algorithm itself) may provide a default value retrieved from, for example, a machine learning parameter store. In block 830, the component generates a validation or fitness score for the currently-selected genome by, for example, applying the trained model to a set of validation data and assessing the ability of the trained model to correctly identify or classify subjects from among the validation data. In block 840, the component stores the generated score(s) and/or an aggregation thereof produced for the trained models in association with the currently-selected genome. In block 850, if there are any genomes yet to be scored, then the component selects the next genome and loops back to block 810, else the component continues at block 860. In blocks 860 through 890, the component assesses the score generated for each genome and selects the "best" genomes for mutation. In this example, the "best" genomes are those that produce validation or fitness scores that exceed a fitness threshold. In decision block 870, if the score generated for the currently-selected genome exceeds a fitness threshold, then the component continues at block 880, else the component continues at block 890. In block 880, the component flags the currently-selected genome for mutation. In some embodiments, the component may select genomes for mutation based on criteria other than, or in addition to, fitness scores. For example, the component may use novelty scores or other scores to select genomes for mutation. In some cases, the component may employ a tournament selection process in which a number of genomes are randomly selected from the population and the genome with the highest score among this "tournament" is selected for reproduction. In this example, if only low scoring genomes appear in a tournament, a low-scoring genome will be selected for reproduction. In block 890, if there are any genomes yet to be processed, then the component selects the next genome and loops back to block 860, else the component returns the flagged genomes and processing of the component completes.

From the foregoing, it will be appreciated that specific embodiments of the disclosed technology have been described herein for purposes of illustration, but that various modifications may be made without deviating from the scope of the disclosed technology. For example, the disclosed techniques can be applied to fields outside of the medical field, such as predicting weather patterns, geological activity, or any other field in which predictions are made based on sampled input data. To reduce the number of claims, certain aspects of the disclosed technology are presented below in certain claim forms, but applicants contemplate the various aspects of the disclosed technology in any number of claim forms. Accordingly, the disclosed technology is not limited except as by the appended claims.

We claim:

1. A system, having a memory and a processor, for discovering machine learning genomes the system comprising:
   a first component configured to generate a plurality of genomes, wherein each genome identifies at least one feature and at least one parameter for at least one machine learning algorithm, wherein generating a first genome of the plurality of genomes comprises:
      randomly selecting, from among a set of features, one or more of the features,
      randomly selecting, from among a set of parameters for at least one machine learning algorithm, one or more of the parameters, and
      assigning at least one random value to each of the selected parameters;
   a second component configured to, for each generated genome,
      train one or more models using the generated genome, and
      for each model trained using the generated genome, calculate a fitness score for the trained model at least in part by applying the trained model to a validation data set, and
      produce a fitness score for the generated genome based at least in part on the fitness scores calculated for the models trained using the generated genome;
   a third component configured to identify, from among the generated genomes, a plurality of genomes having a fitness score that exceeds a fitness threshold;
   a fourth component configured to for each of the identified genomes, mutate the identified genome; and
   a fifth component configured to identify correlated features from among a first set of features of the first genome at least in part by:
      for each feature of the first set of features,
         applying a feature generator associated with the feature to a training set of data to generate a feature vector for the feature,
      for at least one pair of feature vectors,
         calculating a distance between each feature vector of the pair of feature vectors,
         determining that the calculated distance is less than a distance threshold, and
         in response to determining that the calculated distance is less than the distance threshold, removing, from the first genome, a feature corresponding to at least one feature vector of the pair of feature vectors,
            wherein each feature vector includes, for each of a plurality of patients, a single value generated by applying a first feature generator to at least one representation of physiological data representative of the patient,
   wherein at least one of the components comprises computer-executable instructions stored in the memory for execution by the system.

2. The system of claim 1, wherein the removing, from the first genome, of at least one feature corresponding to at least one feature vector of a first pair of feature vectors comprises:
   randomly selecting one feature vector of the first pair of feature vectors,
   identifying, from among the features of the first genome, a feature corresponding to the randomly selected feature vector; and
   removing, from the first genome, the identified feature.

3. The system of claim 1, further comprising:
   a machine configured to receive physiological signal data from at least one patient;
   a sixth component configured to, for each patient,
      apply at least one of the trained models to at least a portion of the physiological signal data received for the patient by the machine, and
      generate a prediction for the patient based at least in part on the application of the at least one of the trained models to at least a portion of the received physiological signal.

4. The system of claim 1, wherein generating the first genome further comprises:
   randomly determining a first number of features to include in the first genome.

5. The system of claim 4, wherein generating a second genome of the plurality of genomes comprises:
   randomly determining a second number of features to include in the second genome, wherein the randomly determined first number of features to include in the first genome is different from the randomly determined second number of features to include in the second genome.

6. The system of claim 1, wherein the fourth component is configured to mutate a first identified genome having a first number of features at least in part by removing at least one feature so that the mutated first identified genome has a second number of features that is different from the first number of features and is further configured to mutate a second identified genome having a third number of features at least in part by adding at least one feature so that the mutated second identified genome has a fourth number of features that is different from the third number of features and the second number of features.

7. A computer-readable medium storing instructions that, if executed by a computing system having a memory and a processor, cause the computing system to perform a method for discovering machine learning genomes, the method comprising:
generating a plurality of genomes, wherein each genome identifies at least one feature and at least one parameter for at least one machine learning algorithm;
for each generated genome,
training at least one model using the generated genome, and
producing a fitness score for the generated genome based at least in part on the trained at least one model;
identifying, from among the generated genomes, one or more genomes having a fitness score that exceeds a fitness threshold; and
mutating each identified genome,
wherein mutating a first identified genome having a first number of features comprises removing at least one feature so that the mutated first identified genome has a second number of features that is different from the first number of features and wherein mutating a second identified genome having a third number of features comprises adding at least one feature so that the mutated second identified genome has a fourth number of features that is different from the third number of features and the second number of features.

8. The computer-readable medium of claim 7, the method further comprising:
computing the fitness threshold at least in part by, determining an overall fitness score based on the fitness scores produced for each of the generated genomes.

9. The computer-readable medium of claim 7, the method further comprising:
computing the fitness threshold at least in part by, determining a n-th percentile of fitness scores based on the fitness scores produced for each of the generated genomes.

10. The computer-readable medium of claim 7, the method further comprising:
computing the fitness threshold at least in part by, determining an n-th highest fitness score from among the fitness scores produced for each of the generated genomes.

11. The computer-readable medium of claim 7, further comprising:
for each model trained using a first genome,
calculating a fitness score for the model trained using the first genome; and
aggregating the fitness scores calculated for the models trained using the first genome.

12. The computer-readable medium of claim 11, wherein aggregating the fitness scores calculated for the models trained using the first genome comprises calculating an average value of the fitness scores calculated for the models trained using the first genome.

13. The computer-readable medium of claim 7, the method further comprising:
for each mutated genome,
training at least one model using the mutated genome, and
producing a fitness score for the mutated genome based at least in part on the at least one model trained using the mutated genome.

14. The computer-readable medium of claim 7, wherein generating a first genome of the plurality of genomes comprises:
randomly determining a fifth number of features to include in the first genome;
randomly selecting, from among a set of features, the randomly determined fifth number of features to include in the first genome;
randomly selecting, from among a set of parameters for at least one machine learning algorithm, one or more of the parameters, wherein at least one of the selected parameters identifies a machine learning algorithm from among a plurality of machine learning algorithms, and
wherein mutating at least one identified genome includes mutating a parameter for at least one machine learning algorithm.

15. A method, performed by a computing system having a memory and a processor, for discovering machine learning genomes, the method comprising:
generating, with the processor, a plurality of genomes, wherein each genome identifies at least one feature and at least one parameter for at least one machine learning algorithm;
for each generated genome,
training at least one model using the generated genome, and
producing a fitness score for the generated genome based at least in art on the trained at least one model;
identifying, from among the generated genomes at least one genome having a fitness score that exceeds a fitness threshold; and
mutating each identified genome,
wherein mutating a first identified genome having a first number of features comprises removing at least one feature so that the mutated first identified genome has a second number of features that is different from the first number of features and wherein mutating a second identified genome having a third number of features comprises adding at least one feature so that the mutated second identified genome has a fourth number of features that is different from the third number of features and the second number of features.

16. The method of claim 15, wherein generating a first genome of the plurality of genomes comprises:
randomly selecting, from among a set of features, one or more of the features;
randomly selecting, from among a set of parameters for at least one machine learning algorithm, one or more of the parameters; and
assigning at least one value to each of the selected parameters.

17. The method of claim 16, wherein generating the first genome further comprises:
for each feature of the randomly selected features,
retrieving a feature vector for the feature based at least in part on a feature generator associated with the feature and a training set of data;
identifying pairs of correlated feature vectors from among the retrieved feature vectors; and
for each identified pair of correlated feature vectors,
identifying one feature vector of the pair of correlated feature vectors, removing, from the first genome, the feature associated with the feature generator used to generate the identified feature vector;
randomly selecting, from among the set of features, a feature to add to the first genome, and
adding the randomly selected feature to the first genome.

18. The method of claim 17, wherein identifying pairs of correlated feature vectors comprises:
for each pair of feature vectors,
calculating a distance metric for the pair of feature vectors, and
determining whether the distance metric calculated for the pair of feature vectors is less than a distance threshold,
wherein the distance threshold is determined based at least in part on the calculated distance metrics determined for each pair of feature vectors.

19. The method of claim 15, wherein mutating a third identified genome comprises:
selecting at least one feature of the third identified genome; and
removing, from the third identified genome, each of the selected features of the third identified genome.

20. The method of claim 15, wherein mutating a third identified genome comprises:
randomly selecting, from among the set of features, a plurality of the features; and
adding, to the third identified genome, each of the randomly selected plurality of features.

21. The method of claim 15, wherein mutating a third identified genome comprises:
modifying at least one feature of the third identified genome.

22. The method of claim 15, wherein mutating a third identified genome comprises:
modifying at least one machine learning algorithm parameter of the first identified genome.

23. The method of claim 15, wherein generating a first genome of the plurality of genomes comprises:
randomly determining a fifth number of features to include in the first genome;
randomly selecting, from among a set of features, the randomly determined fifth number of features to include in the first genome;
randomly selecting, from among a set of parameters for at least one machine learning algorithm, one or more of the parameters, wherein at least one of the selected parameters identifies a machine learning algorithm from among a plurality of machine learning algorithms.

24. The method of claim 15, wherein mutating at least one identified genome includes mutating a parameter for at least one machine learning algorithm.

25. A method, performed by a computing system having a memory and a processor, for discovering machine learning genomes, the method comprising:
generating a plurality of genomes, wherein each genome identifies at least one feature and at least one parameter for at least one machine learning algorithm, wherein generating a first genome of the plurality of genomes comprises:
randomly selecting, from among a set of features, one or more of the features,
randomly selecting, from among a set of parameters for at least one machine learning algorithm, one or more of the parameters, and
assigning at least one random value to each of the selected parameters;
for each generated genome,
training one or more models using the generated genome, and
for each model trained using the generated genome,
calculating a fitness score for the trained model at least in part by applying the trained model to a validation data set, and
producing a fitness score for the generated genome based at least in part on the fitness scores calculated for the models trained using the generated genome;
identifying, from among the generated genomes, a plurality of genomes having a fitness score that exceeds a fitness threshold;
for each of the identified genomes, mutating the identified genome; and
identifying correlated features from among a first set of features of the first genome at least in part by:
for each feature of the first set of features,
applying a feature generator associated with the feature to a training set of data to generate a feature vector for the feature,
for at least one pair of feature vectors,
calculating a distance between each feature vector of the pair of feature vectors,
determining that the calculated distance is less than a distance threshold, and
in response to determining that the calculated distance is less than the distance threshold, removing, from the first genome, a feature corresponding to at least one feature vector of the pair of feature vectors,
wherein each feature vector includes, for each of a plurality of patients, a single value generated by applying a first feature generator to at least one representation of physiological data representative of the patient.

26. The method of claim 25, wherein mutating a first identified genome having a first number of features comprises removing at least one feature so that the mutated first identified genome has a second number of features that is different from the first number of features and wherein mutating a second identified genome having a third number of features comprises adding at least one feature so that the mutated second identified genome has a fourth number of features that is different from the third number of features and the second number of features.

* * * * *

UNITED STATES PATENT AND TRADEMARK OFFICE
CERTIFICATE OF CORRECTION

PATENT NO. : 11,062,792 B2
APPLICATION NO. : 15/653441
DATED : July 13, 2021
INVENTOR(S) : Grouchy et al.

Page 1 of 3

It is certified that error appears in the above-identified patent and that said Letters Patent is hereby corrected as shown below:

On the Title Page

Item (56), in Column 2, under "Other Publications", Line 1, delete "Generration" and insert -- Generation --, therefor.

On the page 3, in Column 2, under "Other Publications", Line 7, delete "18834730_6," and insert -- 18834730.6, --, therefor.

On the page 3, in Column 2, under "Other Publications", Line 10, delete "7,'Omputing;" and insert -- Computing; --, therefor.

On the page 3, in Column 2, under "Other Publications", Line 11, delete "APPLICATIONS_" and insert -- Applications. --, therefor.

On the page 3, in Column 2, under "Other Publications", Line 14, delete "_earning" and insert -- Learning --, therefor.

On the page 3, in Column 2, under "Other Publications", Line 16, delete "Nietvvorks" and insert -- Networks --, therefor.

On the page 3, in Column 2, under "Other Publications", Line 17, delete ")(P032604443." and insert -- XP032604443. --, therefor.

On the page 3, in Column 2, under "Other Publications", Line 18, delete "3HARDWAJ" and insert -- Bhardwaj --, therefor.

On the page 3, in Column 2, under "Other Publications", Line 25, delete "roceedings" and insert -- Proceedings --, therefor.

Signed and Sealed this
Ninth Day of November, 2021

Drew Hirshfeld
*Performing the Functions and Duties of the
Under Secretary of Commerce for Intellectual Property and
Director of the United States Patent and Trademark Office*

On the page 3, in Column 2, under "Other Publications", Line 27, delete "ages" and insert -- Pages --, therefor.

On the page 3, in Column 2, under "Other Publications", Line 28, delete ".cs.uctedu/" and insert -- .cs.ucf.edu/ --, therefor.

On the page 3, in Column 2, under "Other Publications", Line 29, delete ":retrieved" and insert -- (retrieved --, therefor.

On the page 3, in Column 2, under "Other Publications", Line 30, delete "Nsir" and insert -- Asir --, therefor.

On the page 3, in Column 2, under "Other Publications", Line 31, delete "HighlAmensionaiData,"" and insert -- High-Dimensional Data," --, therefor.

On the page 3, in Column 2, under "Other Publications", Line 31, delete "-Intemational" and insert -- International --, therefor.

On the page 3, in Column 2, under "Other Publications", Line 31, delete "3omputer" and insert -- Computer --, therefor.

On the page 3, in Column 2, under "Other Publications", Line 34, delete "https-J/" and insert -- https:// --, therefor.

On the page 3, in Column 2, under "Other Publications", Line 34, delete "_net/" and insert -- .net/ --, therefor.

On the page 3, in Column 2, under "Other Publications", Line 35, delete "Danasingh/ Dublication/" and insert -- Danasingh/Publication/ --, therefor.

On the page 3, in Column 2, under "Other Publications", Line 36, delete "Methods _for High" and insert -- Methods_for_High --, therefor.

On the page 3, in Column 2, under "Other Publications", Line 36, delete "Dimensional Data/ inks/" and insert -- Dimensional_Data/links/ --, therefor.

On the page 3, in Column 2, under "Other Publications", Line 37, delete "fLiterature" and insert -- /Literature --, therefor.

In the Specification

In Column 8, Line 8, delete "F2n=" and insert -- $F2_n=$ --, therefor.

In the Claims

In Column 21, Line 40, in Claim 1, delete "genomes" and insert -- genomes, --, therefor.

CERTIFICATE OF CORRECTION (continued)
U.S. Pat. No. 11,062,792 B2

In Column 22, Line 1, in Claim 1, delete "to" and insert -- to, --, therefor.

In Column 24, Line 33, in Claim 15, delete "art" and insert -- part --, therefor.

In Column 24, Line 34, in Claim 15, delete "genomes" and insert -- genomes, --, therefor.